(12) United States Patent
Ingham et al.

(10) Patent No.: US 11,340,157 B2
(45) Date of Patent: May 24, 2022

(54) METHODS OF SPECTROSCOPIC ANALYSIS

(71) Applicant: The University of Liverpool, Liverpool Merseyside (GB)

(72) Inventors: James Joseph Ingham, Liverpool (GB); Stephen David Barrett, Liverpool (GB); Peter Weightman, Liverpool (GB)

(73) Assignee: The University of Liverpool, Liverpool Merseyside (GB)

( * ) Notice: Subject to any disclaimer, the term of this patent is extended or adjusted under 35 U.S.C. 154(b) by 0 days.

(21) Appl. No.: 17/046,681

(22) PCT Filed: Apr. 5, 2019

(86) PCT No.: PCT/GB2019/050998
§ 371 (c)(1),
(2) Date: Oct. 9, 2020

(87) PCT Pub. No.: WO2019/197806
PCT Pub. Date: Oct. 17, 2019

(65) Prior Publication Data
US 2021/0148813 A1    May 20, 2021

(30) Foreign Application Priority Data
Apr. 11, 2018 (GB) .................................... 1806002

(51) Int. Cl.
*G01N 21/3563* (2014.01)
*G01N 33/483* (2006.01)
*G01N 33/574* (2006.01)

(52) U.S. Cl.
CPC ..... *G01N 21/3563* (2013.01); *G01N 33/4833* (2013.01); *G01N 33/57407* (2013.01)

(58) Field of Classification Search
CPC .......... G01N 21/3563; G01N 33/4833; G01N 33/57407
See application file for complete search history.

(56) References Cited

U.S. PATENT DOCUMENTS 9,025,850 B2   5/2015   Diem et al.
9,047,662 B2   6/2015   Diem et al.
(Continued)

FOREIGN PATENT DOCUMENTS

JP   2011522260 A   7/2011
JP   2013533960 A   8/2013
(Continued)

OTHER PUBLICATIONS

Bulgakova, N. et al., "In Vivo Local Fluorescence Spectroscopy in PDD of Superficial Bladder Cancer", Medical Laser Application, vol. 24 No. 4, Dec. 5, 2009, pp. 247-255, Elsevier.
(Continued)

*Primary Examiner* — Maurice C Smith
(74) *Attorney, Agent, or Firm* — Coats + Bennett, PLLC

(57) ABSTRACT

A method of selecting wavelengths of radiation for discriminating a first cell or tissue type from a different cell or tissue type is described. First and second sets of absorption spectra are obtained, each set comprising spectra obtained at a plurality of different spatial regions of the first cell or tissue type and of the different cell or tissue type, respectively. Sets of corresponding metrics are defined for the first and second sets of absorption spectra for each spatial region. Each metric comprises information corresponding to the absorption for at least two different wavelengths. The metrics in each set comprise different combinations of wavelengths. A characteristic value is generated for each metric. Distributions are generated for each metric using corresponding characteristic values for the first cell or tissue type and for the different cell or tissue type and compared to determine
(Continued)

an extent of similarity. The metrics are ranked based on the extent of similarity and wavelengths associated with higher ranked metrics, having higher similarities, are selected.

20 Claims, 18 Drawing Sheets

(56) References Cited

U.S. PATENT DOCUMENTS

| | | | |
|---|---|---|---|
| 9,606,057 | B2 | 3/2017 | Kapelushnik et al. |
| 2012/0103817 | A1 | 5/2012 | Omori et al. |
| 2016/0317035 | A1 | 11/2016 | Hendriks et al. |
| 2017/0140299 | A1 | 5/2017 | Tanji |

FOREIGN PATENT DOCUMENTS

| | | | | |
|---|---|---|---|---|
| JP | 2015102542 | A | 6/2015 | |
| JP | 2016028229 | A | 2/2016 | |
| JP | 2017015724 | A | 1/2017 | |
| WO | 2012059748 | A1 | 5/2012 | |
| WO | 2017161097 | A1 | 9/2017 | |
| WO | WO-2017161097 | A1 * | 9/2017 | ......... G01N 21/3563 |

OTHER PUBLICATIONS

Gupta, S. et al., "Wavelet-Based Characterization of Spectral Fluctuations in Normal, Benign, and Cancerous Human Breast Tissues", Journal of Biomedical Optics, vol. 10 No. 5, Sep. 1, 2005, pp. 054012-1-054012-9, SPIE.

Cothren, R. et al., "Detection of Dysplasia at Colonoscopy Using Laser-Induced Fluorescence: A Blinded Study", Gastrointestinal Endoscopy, vol. 44 No. 2, Aug. 1, 1996, pp. 168-176, American Society of Gastrointestinal Endoscopy.

Katzilakis, N. et al., "Spectral Characteristics of Acute Lymphoblastic Leukemia in Childhood", Leukemia Research, vol. 28 No. 11, Nov. 1, 2004, pp. 1159-1164, Elsevier.

* cited by examiner

US 11,340,157 B2

METHODS OF SPECTROSCOPIC ANALYSIS

FIELD OF THE INVENTION

The present invention relates to the analysis of radiation absorption data and particularly methods of selecting wavelengths that are capable of distinguishing one cell or tissue type from a different cell or tissue type.

BACKGROUND

Absorption spectroscopy is an important tool in the diagnosis of disease. For example, Fourier transform infrared (FTIR) spectroscopy is one of the most successful infrared imaging techniques applied to studies of cancer. Known methods of analysing the large data sets output from FTIR use techniques such as principal component analysis and the random forest analysis. These techniques involve the identification of radiative absorption 'fingerprints' for characterizing different samples. When used for identifying the presence or absence of a given cell or tissue type (e.g. a cancerous cell or tissue type) in a sample taken from a patient, these techniques are known to result in false positives and/or fail to identify the presence of the cell or tissue type. Such failures can be very damaging to the patient and could result in unnecessary and potentially harmful treatment being performed and/or a lack of treatment when treatment is needed. It is desirable to increase the accuracy of diagnosis and/or reduce a frequency of false positives. It is also desirable to provide methods of analysing absorption spectra data which deliver high degrees of accuracy via less intensive data processing compared to prior art methods.

It is desirable to provide a method of selecting discriminating wavelengths for use in absorption spectroscopy that obviates or mitigates one or more problems of the prior art whether identified herein or elsewhere.

SUMMARY OF THE INVENTION

The invention analyses data obtained from radiation absorption spectroscopy performed on different cell or tissue types. The invention is able to select wavelengths of radiation at which distinguishing radiation absorption fingerprints are found for the different cell or tissue types. The selected wavelengths are thus able to discriminate one cell or tissue type from another cell or tissue type with a high degree of accuracy. To exemplify the utility of the method, the invention has been shown to discriminate four different cell types and four different tissue types with accuracies greater than known methods with less intensive data processing being used. The invention may be used to improve an accuracy of the diagnosis of diseases.

According to a first aspect there is provided a method of selecting wavelengths of radiation capable of discriminating a first cell or tissue type from a different cell or tissue type for use in radiation absorption spectroscopy, the method comprising obtaining a first set of absorption spectra comprising an absorption spectrum obtained at each spatial region of a plurality of different spatial regions of the first cell or tissue type and obtaining a second set of absorption spectra comprising an absorption spectrum obtained at each spatial region of a plurality of different spatial regions of the different cell or tissue type, defining a set of metrics for each spatial region belonging to the first set of absorption spectra and defining a corresponding set of metrics for each spatial region belonging to the second set of absorption spectra, wherein each metric comprises information corresponding to the quantities of radiation absorbed for at least two different wavelengths for the given spatial region and wherein the metrics in a set comprise different combinations of wavelengths, performing a first mathematical function on each metric to generate a characteristic value for each metric, wherein the characteristic value is dependent on the amount of radiation absorbed at each of the at least two different wavelengths belonging to the metric, generating a distribution comprising the characteristic values of a given metric across the plurality of spatial regions belonging to the first cell or tissue type, generating a corresponding distribution comprising the characteristic values of the same given metric across the plurality of spatial regions belonging to the different cell or tissue type and repeating for each of the metrics, comparing the distributions generated for the first cell or tissue type and the different cell or tissue type for a given metric, determining an extent of similarity between the distributions, and repeating this step for each of the other metrics, ranking the metrics based on the extent of similarity between the distributions belonging to the metrics, wherein metrics associated with distributions having less similarity rank higher than metrics associated with distributions having more similarity, and selecting the wavelengths of radiation associated with the higher ranked metrics. The cells or tissues used to obtain the respective absorption spectra (i.e. the first set of absorption spectra comprising an absorption spectrum obtained at each spatial region of a plurality of different spatial regions of the first cell or tissue type and the second set of absorption comprising an absorption spectrum obtained at each spatial region of a plurality of different spatial regions of the different cell or tissue type) are typically provided as samples obtained from a patient. The respective first tissue type and different cell or tissue type may have been obtained from a patient separately or they may be from a single cell or tissue sample obtained from a patient (e.g. both cell or tissue types may be present in the same biopsy).

That is, the method according to the first aspect defines a machine learning approach to efficiently identify (i.e. select) wavelengths of radiation, associated with higher ranked metrics, that discriminate (i.e. distinguish) between the first cell or tissue type and the different cell or tissue type, without requiring prior biological and/or chemical knowledge of the cells or tissue types and/or without bias. Particularly, this machine learning approach generates and compares the distributions for the characteristic values of the metrics for the absorption spectra obtained from a plurality of different spatial regions of the cells or tissues types, thereby considering around $10^{11}$ data points. In contrast, conventional methods consider at most $10^4$ to $10^5$ data points. In this way, for example, by using the thus identified wavelengths, cancer associated myofibroblasts (CAMs) may be more effectively distinguished from normal tissue adjacent to cancer (ATMs), allowing earlier diagnosis and improved patient outcome.

The method according to the first aspect has been advantageously found to provide discriminating wavelengths that can be used to distinguish one cell or tissue type from one or more other cell or tissue types with a high degree of accuracy. In some cases, the method has discovered diagnostic wavelengths that have not been found using known techniques. The method has been shown to discriminate, with accuracies in the range of about 81% to about 97%, between FTIR images of esophageal cancer OE19, OE21, cancer associated myofibroblast (CAM) and adjacent tissue myofibroblast (ATM) cell lines. The latter cells are morphologically indistinguishable but are known to have functionally important differences in their capacity to stimulate cancer cell growth; the method according to the first aspect provides the first accurate spectral discrimination between CAM and ATM cells taken from the same patient. The method can discriminate, with accuracies in the range of about 69% to about 93%, between FTIR images of cancerous tissue, cancer associated stroma (CAS), Barrett's tissue and Barrett's associated stroma (BAS) esophageal cancer tissue samples. The method discriminates between different cell and tissue types with a high degree of accuracy and speed and has significant advantages over the known methods such as, for example, the random forest method. Particularly, rapid and accurate discrimination between cell types may be achieved, and key wavenumbers identified which uniquely discriminate between different cell types. This metrics-based analysis (MA) method according to the first aspect is shown to be unique for distinguishing between cancer stromal cells from the same patient. The key wavenumbers differ significantly from those typically found to discriminate between various esophageal cell and tissue types. Further, the method according to the first aspect allows cancer staging based discrimination of the stromal cell types that provide the niche for tumor development. The method is expected to be widely applicable to other cell types and tissues due to the large variety of chemical bonds found in biological samples.

The higher ranked metrics may comprise any desired proportion of the ranked metrics. For example, the higher ranked metrics may comprise the metrics ranked in the top 50% of all metrics. In embodiments, the higher ranked metrics may not include any metrics ranked outside the top 50% of all metrics. As another example, the higher ranked metrics may comprise the metrics ranked in the top 30% of all metrics. In embodiments, the higher ranked metrics may not include any metrics ranked outside the top 30% of all metrics. As a further example, the higher ranked metrics may comprise the metrics ranked in the top 10% of all metrics. In embodiments, the higher ranked metrics may not include any metrics ranked outside the top 10% of all metrics. The higher ranked metrics may, for example, comprise the metrics ranked in the top 5% of all metrics. In embodiments, the higher ranked metrics may not include any metrics ranked outside the top 5% of all metrics. The metrics may be ranked in accordance with an area of overlap between the distributions. The metrics may be ranked according to an outcome of the following equation:

$$n = \frac{1 - \text{Area of overlap between the distributions}}{\text{Total area of the distributions}}$$

The distributions may be treated as probability distribution functions. The metrics may be ranked by quantifying the extent of similarity between the probability distribution functions. In one preferred embodiment, the extent of similarity between the probability distribution functions is quantified by using parameters of the probability distribution functions.

In an embodiment, the first cell or tissue type may be known and a first portion of spatial regions may not be used to generate the distributions. In such an embodiment, the method may further comprise defining a success rate for each higher ranked metric, the success rates being determined by using the higher ranked metrics to allocate each spatial region in the first portion of spatial regions to either the first cell or tissue type or the different cell or tissue type, determining the number of spatial regions of the first portion of spatial regions that were correctly allocated using the higher ranked metrics, and calculating the success rate of a higher ranked metric as being how often the higher ranked metric correctly assigned spatial regions of the first portion of spatial regions to either the first cell or tissue type or the different cell or tissue type. The success rate may be calculated for any metric. The success rate may be calculated for each metric. The wavelengths may be selected from metrics having a higher success rate than other metrics. In one preferred embodiment, the wavelengths are selected from the 500 metrics having the highest success rate. In embodiments, the wavelengths are selected only from wavelengths associated with the 500 metrics having the highest success rate. In embodiments, all of the wavelengths associated with the 500 metrics having the highest success rate are selected. The wavelengths may, for example, be selected from up to the 300 metrics having the highest success rate. In embodiments, the wavelengths are selected only from wavelengths associated with the 300 metrics having the highest success rate. All of the wavelengths associated with the 300 metrics having the highest success rate may be selected. The wavelengths may, for example, be selected from up to 100 metrics having the highest success rate. In embodiments, the wavelengths are selected only from wavelengths associated with the 100 metrics having the highest success rate. All of the wavelengths associated with the 100 metrics having the highest success rate may be selected. The wavelengths may, for example, be selected from up to 50 metrics, 40 metrics, 30 metrics, 20 metrics or 10 metrics having the highest success rate. In embodiments, only wavelengths associated with the 50 metrics having the highest success rate are selected. All of the wavelengths associated with the 50 metrics having the highest success rate may be selected. The wavelengths may be selected from up to 5 metrics having the highest success rate. In embodiments, the wavelengths are selected only from wavelengths associated with the 5 metrics having the highest success rate. All of the wavelengths associated with the 5 metrics having the highest success rate may be selected.

Leaving some of the data to test the discrimination accuracy of the selected wavelengths advantageously enables an evaluation of how well the metrics can discriminate the different cell or tissue types, thus providing more information from which to select the discriminating wavelengths.

The characteristic values for the first portion of spatial regions may be compared with the probability density functions in order to allocate each of the spatial regions of the first portion to either the first cell or tissue type or the different cell or tissue type.

The method may further comprise defining a mislabelling rate for each higher ranked metric, the mislabelling rate being the probability that the higher ranked metric identified the different cell or tissue type as being the first cell or tissue type. The mislabelling rate may be calculated for any metric or group of metrics. The mislabelling rate may be calculated for each metric. The wavelengths may be selected from metrics having lower mislabelling rates than other metrics. The wavelengths may be selected from up to 500 metrics having the lowest mislabelling rate. In embodiments, only wavelengths associated with the 500 metrics having the lowest mislabelling rate are selected. All of the wavelengths associated with the 500 metrics having the lowest mislabelling rate may be selected. The wavelengths may be selected from up to 300 metrics having the lowest mislabelling rate. In embodiments, only wavelengths associated with the 300 metrics having the lowest mislabelling rate may be selected. All of the wavelengths associated with the 300 metrics having the lowest mislabelling rate may be selected. The wavelengths may be selected from up to 100 metrics having the lowest mislabelling rate. In embodiments, only wavelengths associated with the 100 metrics having the lowest mislabelling rate are selected. All of the wavelengths associated with the 100 metrics having the lowest mislabelling rate may be selected. The wavelengths may be selected from up to the 50 metrics, 40 metrics, 30 metrics, 20 metrics or 10 metrics having the lowest mislabelling rate. In embodiments, only wavelengths associated with the 50 metrics having the lowest mislabelling rate are selected. All of the wavelengths associated with the 50 metrics having the lowest mislabelling rate may be selected. The wavelengths may be selected from up to 5 metrics having the lowest mislabelling rate. In embodiments, only wavelengths associated with the 5 metrics having the lowest mislabelling rate are selected. All of the wavelengths associated with the 5 metrics having the lowest mislabelling rate may be selected.

Defining a mislabelling rate advantageously provides further information on which of the selected wavelengths are more accurate for discrimination of the different cell or tissue types. The method may further comprise scoring the higher ranked metrics by performing a second mathematical function on the calculated success rates and mislabelling rates and comparing outcomes of the second mathematical function. Any metric or group of metrics may be scored. Each metric may be scored. The wavelengths may be selected from metrics having higher scores than other metrics. The wavelengths may be selected from the top 500 scoring metrics. In embodiments, only wavelengths associated with the top 500 scoring metrics are selected. The wavelengths may be selected from the top 300 scoring metrics. In embodiments, only wavelengths associated with the top 300 scoring metrics are selected. The wavelengths may be selected from the top 100 scoring metrics. In embodiments, only wavelengths associated with the top 100 scoring metrics are selected. The wavelengths may be selected from the top 50 scoring metrics. In embodiments, only wavelengths associated with the top 50 scoring metrics are selected. The wavelengths may be selected from the top 5 scoring metrics. In embodiments, only wavelengths associated with the top 5 scoring metrics are selected.

Scoring the metrics advantageously provides a further insight into which of the selected wavelengths are more accurate for discrimination of the different cell or tissue types.

The second mathematical function may be:

$$score = success\ rate \times (1 - mislabeling\ rate)$$

This equation was found to be highly useful as a second mathematical function for accurately scoring the metrics.

The method may further comprise determining aggregate success rates for a plurality of combinations of the higher ranked metrics, the aggregate success rates being calculated by using the allocations of the first portion of spatial regions associated with two of the highest ranked metrics to determine an average allocation of the first portion of spatial regions and determining an aggregate success rate associated with the average allocation by determining how often the average allocation is correct, and repeating this step using an increasing number of the higher ranked metrics. Aggregate success rates may be determined for a plurality of combinations of any of the metrics. Aggregate success rates may be determined for all combinations of the metrics.

Determining an aggregate success rate for an increasing number of metrics advantageously provides an overview of the total number of metrics that should be utilized to further improve an accuracy of the discrimination between different cell or tissue types.

The method may further comprise comparing each aggregate success rate to the number of metrics used to obtain the aggregate success rate, and selecting a sub-group of wavelengths that are associated with the metrics for which the aggregate success rate is greater than a desired aggregate success rate. An exemplary desired aggregate success rate may be, for instance, 70%. An exemplary desired aggregate success rate may, for instance, be 90%.

Selecting a sub-group of wavelengths based on a comparison of the aggregate success rates advantageously provides a preferred number of metrics (as defined by the user) for the most accurate discrimination of cell types. The user may, for example, choose a balance between computation time and discrimination accuracy by selecting a desired aggregate success rate to be equalled or surpassed using the method. In one preferred embodiment, the number of higher ranked metrics that produce the highest success rate are considered to be the preferred number of metrics to use to achieve greater discrimination accuracy, and wavelengths associated with the preferred number of metrics are selected.

The first mathematical function may determine a ratio between the amounts of radiation absorbed at the at least two different wavelengths of radiation of a metric.

Determining a ratio between the amounts of radiation absorbed at the at least two different wavelengths of radiation of a metric advantageously negates measurement variables such as, for example, a thickness of the samples of the first cell or tissue type and the different cell or tissue type from which the first and second absorption spectra were obtained. This in turn improves a confidence of the selection of the discriminating wavelengths because fewer unwanted variables influence the selection.

The distributions may be treated as probability distribution functions. The metrics may be ranked by quantifying the extent of similarity between the probability distribution functions.

In one preferred embodiment, the wavelengths are selected from up to about 500 of the highest ranking metrics. The wavelengths may be selected from up to about 300 of the highest ranking metrics. The wavelengths may be selected from up to about 100 of the highest ranking metrics. The wavelengths may be selected from up to about 50, 40, 30, 20 or 10 of the highest ranking metrics. The wavelengths may be selected from up to about 5 of the highest ranking metrics.

The portion of spatial regions used to generate the first and second distributions may be greater than the portion of spatial regions used to calculate the success rates. In one preferred embodiment, about 75% of the spatial regions from the image of the first cell or tissue type are used to generate the first and second distributions and the remaining spatial regions from the image of the first cell or tissue type are used to determine the success rates. This constitutes a preferred "machine learning" approach which improves confidence of the outcomes of the method.

The wavelengths of radiation used to generate the first and second sets of absorption spectra may be chosen using pre-existing knowledge of the first cell or tissue type's radiation absorption behaviour. This advantageously avoids spending time on areas of the absorption spectrum that are known not to provide any useful information for discriminating the cell or tissue types.

The first and second sets of absorption spectra may comprise wavelengths selected from within the range of about 900 $cm^{-1}$ to about 4000 $cm^{-1}$. The first and second sets of absorption spectra may comprise wavelengths selected from within the range of about 1000 $cm^{-1}$ to about 3000 $cm^{-1}$. In one preferred embodiment, the first and second sets of absorption spectra comprise wavelengths selected from within the range of about 1000 $cm^{-1}$ to about 1800 $cm^{-1}$. For example, the first and second sets of absorption spectra may comprise data obtained at, for example, 6 $cm^{-1}$ intervals in the range of from about 1000 $cm^{-1}$ to about 1800 $cm^{-1}$.

The distributions may be histograms. The histograms may be fitted (i.e. approximated) to a Gaussian distribution.

The fitted Gaussian distributions may be treated as probability density functions and the characteristic values for the first portion of spatial regions may be compared with the probability density functions in order to assign each of the spatial regions of the first portion to either the first cell or tissue type or the different cell or tissue type.

At least one of the first cell or tissue type and/or the different cell or tissue type may be a diseased tissue. The disease may be cancer, i.e. the diseased tissue may be cancerous. In such embodiments, at least one of the other respective first cell or tissue type and/or the different cell or tissue type may be a diseased tissue, e.g. wherein the method is able to discriminate between different types of diseased tissues in a patient sample. The at least one of the other respective first cell or tissue type and/or the different cell or tissue type may be a healthy tissue, e.g. wherein the method is able to discriminate between diseased and healthy tissue in a patient sample.

The first cell or tissue type and the respective different cell or tissue type(s) may be diseased tissue. The first cell or tissue type and the different cell or tissue type may be tissues associated with different diseases, or different stages of the same disease. At least one of the first cell or tissue type and different cell or tissue type may be in a pre-diseased state, or a state that is known to be at risk of developing into diseased state, or causing disease (e.g. a cell or tissue type in a pre-cancerous state).

Cancer

Esophageal cancer is the sixth most common cause of cancer mortality and is the cancer with the fastest rise in incidence in the western world. There are two main forms of esophageal cancer. One is squamous cell carcinoma, which is most common in Asia and is associated with smoking and poor diet. The other is adenocarcinoma, which is more common in the west and is associated with the gastro-esophageal reflux of acid and bile salts and the preneoplastic condition of Barrett's metaplasia of the esophagus. Both cancers consist of malignant epithelial cells and stroma and the latter is important for facilitating cancer progression. One of the most important cell types in the stroma is a specialized fibroblast called the myofibroblast that produces growth factors and cytokines that promote cancer growth and metastasis. The diagnosis of esophageal cancer follows the standard approach of examining images of excised tissue, obtained by endoscopy, after staining with Haematoxylin and Eosin (H&E). This highlights the nucleic acid and protein content of the specimen at blue and red visible wavelengths respectively. Typically, the interobserver discordance for the diagnosis of the low-grade dysplasia, which is characteristic of the earliest preneoplastic stage of disease is greater than 50%. Although this discordance is reduced to ~15% for the diagnosis of the more serious condition of high-grade dysplasia, there is a need to improve the accuracy of diagnosis since false positives can give rise to unnecessary procedures and false negatives can be fatal. As with all cancers, early detection is critical for the best patient outcome and there is a need for cheaper, more accurate and ideally automated methods for cancer diagnosis and for identification of those patients with Barrett's esophagus at most risk of progressing to dysplasia and cancer.

It has long been recognized that expanding the wavelength range of images of tissue will convey more information and there has been considerable progress in the application of infrared (IR) techniques to the examination of tissue in order to exploit the association of particular IR wavelengths with specific chemical moieties. Fourier transform IR (FTIR) spectroscopy is one of the most successful IR imaging techniques applied to studies of cancer and has shown considerable promise for development into a diagnostic tool. Imaging FTIR typically yields information at each pixel in a two-dimensional image at ~1000 wavelengths, with each spectrum containing information on the many excitation modes of the large number of different molecular species contained in the specimen. Most reported work has analyzed these large data sets using techniques such as principal component analysis and the identification of 'fingerprints' for characterizing specimens, rather than at the level of detailed assignments of individual vibrational modes that is possible with simpler molecular systems.

It is now well recognized that tumor formation requires not just the acquisition of DNA mutations by cancer cells but also an appropriate cellular microenvironment (the cancer cell niche) that facilitates tumor growth and metastasis. Different stromal cell types are implicated in niche formation including inflammatory and immune cells, microvascular cells and cells of fibroblastic lineages. Myofibroblasts are an important sub-set of fibroblasts; cancer associated myofibroblasts (CAMs) are morphologically similar to myofibroblasts obtained from macroscopically normal tissue adjacent to cancer (ATMs) but they differ markedly in their biology and in particular are strong stimulants of aggressive behaviors by cancer cells. Transcriptomic, proteomic and miRNA profiling studies have all provided a basis for understanding the functional differences between CAMs and ATMs. However, there remains a pressing need for methods that allow the rapid and precise identification of these cell types not least because this would facilitate the identification of the cellular microenvironments in which tumor formation occurs.

Previous work on the application of IR techniques to the study of esophageal cancer is discussed later. In this paper the results of applying a novel multivariate analysis technique to FTIR spectra are described for two esophageal cancer cell lines, OE19 and OE21, and two esophageal myofibroblast cell lines derived from the stroma of an esophageal adenocarcinoma patient. OE19 was derived from an adenocarcinoma from the esophago-gastric junction and OE21 was derived from a squamous cell esophageal cancer. Both were purchased from HPA Culture Collections and maintained as described previously. The two myofibroblast cell lines were CAMs and ATM obtained from the same patient and previously characterized.

As described herein, the method according to the first aspect is able to discriminate between all four cell types with high accuracy and speed. This is particularly important for CAM and ATM cells in view of the much stronger capacity of the former in stimulating cancer cell growth and invasion. The data therefore support the feasibility of new staging methods for early tumor development based on identifying the presence of those myofibroblasts (CAMs) most likely to facilitate cancer cell growth. Since early diagnosis improves patient outcomes this approach should bring clear benefits.

The disease may be cancer, i.e. the diseased tissue may be cancerous or the pre-diseased tissue may be at risk of becoming cancerous. At least one of the first cell or tissue type and the different cell or tissue type may be cancerous, e.g. wherein the first cell or tissue type and the respective different cell or tissue type are cancerous, e.g. cancer associated myofibroblast cells. The cancer may be esophageal cancer, such as cancer associated with esophageal cancer cell line OE19 and/or OE21.

The disease may be gastroesophageal reflux disease, e.g. Barrett's esophagus. The diseased tissue may for instance be Barrett's tissue or Barrett's stroma.

In one preferred embodiment, the first and second sets of absorption spectra are obtained using Fourier transform infrared spectroscopy.

The first and second sets of absorption spectra may be corrected for Mie scattering effects.

According to a second aspect there is provided a method of discriminating between multiple different cell or tissue types comprising performing absorption spectroscopy on the multiple different cell or tissue types using wavelengths of radiation selected according to the method of the first aspect or any of its associated options, and determining respective characteristic values for the multiple cell or tissue types according to the steps described in the first aspect (or any embodiment thereof), comparing the characteristic values obtained by the absorption spectroscopy with distributions corresponding to known cell or tissue types obtained by the method of the first aspect or any of its associated options, and determining whether or not the characteristic values obtained by the absorption spectroscopy performed on the multiple different cell or tissue types correspond to the known distributions for the known cell or tissue types. The cells or tissues used to obtain the respective absorption spectra are typically provided as samples obtained from a patient. The respective first tissue type and different cell or tissue type may have been obtained from a patient separately or they may be from a single cell or tissue sample obtained from a patient (e.g. both cell or tissue types may be present in the same biopsy).

According to a third aspect there is provided a method of discriminating between multiple different cell or tissue types comprising obtaining information corresponding to the quantity of radiation absorbed at each of a plurality of wavelengths of radiation selected according to the method of the first aspect or any of its associated options/embodiments for the multiple different cell or tissue types and determining respective characteristic values for the multiple cell or tissue types according to the steps described in the first aspect of the invention, comparing the characteristic values obtained at each of the plurality of wavelengths for the multiple cell or tissue types with distributions corresponding to known cell or tissue types obtained by the method of the first aspect or any of its associated options that are associated with the selected wavelengths, and determining whether or not the characteristic values for each respective cell or tissue type correspond with the known distributions for the known cell or tissue types. The cells or tissues used to obtain the respective absorption spectra are typically provided as samples obtained from a patient. The respective first tissue type and different cell or tissue type may have been obtained from a patient separately or they may be from a single cell or tissue sample obtained from a patient (e.g. both cell or tissue types may be present in the same biopsy).

Obtaining information corresponding to the quantity of radiation absorbed at each of a plurality of wavelengths of radiation may comprise performing radiation spectroscopy on the multiple different cell or tissue types.

According to a fourth aspect there is provided a method of identifying the presence or absence of a first cell or tissue type in a cell or tissue sample obtained from a patient comprising multiple different cell or tissue types, the method comprising obtaining information corresponding to the quantity of radiation absorbed at each of a plurality of wavelengths of radiation selected according to the method of the first aspect and determining respective characteristic values for one or more of the cell or tissue types in the tissue sample according to the steps described in the first aspect of the invention, comparing the characteristic values obtained at each of the plurality of wavelengths for the respective cell or tissue types in the tissue sample (i.e. the cell or tissue types for which the respective characteristic values have been determined) with corresponding known distributions for the first cell or tissue type associated with the selected wavelengths, determining whether or not the characteristic values for the cell or tissue types in the tissue sample correspond with the known distributions for the first cell or tissue type, and, when the characteristic values for the cell or tissue types in the tissue sample are determined to correspond with the known distributions for the first cell or tissue type, identifying the presence of the first cell or tissue type, or when the characteristic values for the cell or tissue types in the tissue sample do not correspond with the known distributions for the first cell or tissue type, determining there to be an absence of the first cell or tissue type. The respective first tissue type and one or more different cell or tissue types may have been obtained from a patient separately or they may be from a single cell or tissue sample obtained from a patient (e.g. both cell or tissue types may be present in the same biopsy).

Where at least one of the first cell or tissue type and the different cell or tissue type is identified as being a diseased tissue, the method (e.g. as described in the fourth aspect of the invention) may further comprise treating the identified disease in the patient, e.g. by therapy or surgery, such as by administering to the patient one or more therapeutic agents having efficacy in treating the disease, i.e. wherein the one or more therapeutic agents are administered in a therapeutically effective amounts. In other words, the present disclosure also provides a method of treating a disease in a patient comprising performing the method of identifying the presence or absence of a first cell or tissue type in a cell or tissue sample obtained from a patient comprising multiple different cell or tissue types according to the fourth aspect (or any embodiments thereof), and in the event that at least one of the first cell or tissue type and the different cell or tissue type is identified as being in a diseased or pre-diseased state, treating the respective disease in the patient (e.g. by therapy or surgery, such as by administering one or more therapeutic agents having efficacy in treating the disease to the patient, i.e. in therapeutic amounts). Where the identified cell or tissue type is attributed with a cell or tissue type that is in a pre-diseased state, or a state that is known to be at risk of developing into diseased state, or causing disease (e.g. a cell or tissue type in a pre-cancerous state), the method may comprise prophylactically treating the patient (i.e. in an attempt to prevent development or further development of the disease). In some embodiments, the method does not further comprise treating the identified disease in the patient, e.g. by surgery or therapy. In embodiments, where at least one of the first cell or tissue type and the different cell or tissue type is a diseased tissue, the method may further comprise contacting the diseased cell or tissue type with an active agent (e.g. therapeutic agent) in vitro, such as with a therapeutic agent known to have efficacy in treating the disease, or an agent that is determined to be a therapeutic candidate for treating the disease.

Wavelengths of radiation selected according to an embodiment may be used to identify a presence or absence of a given cell or tissue type in a sample only containing a single cell or tissue type. This may be achieved by, for example, comparing the characteristic values obtained at each of the wavelengths for the given cell or tissue type in the tissue sample with corresponding known distributions for the given cell or tissue type associated with the selected wavelengths, and determining whether or not the characteristic values for the given cell or tissue type in the tissue sample correspond with the known distributions.

In the above aspects and embodiments, the first cell or tissue type may be esophageal cancer cell line OE19. The first cell or tissue type may be esophageal cancer cell line OE21. The first cell or tissue type may be cancer associated myofibroblast cells. The first cell or tissue type may be adjacent tissue myofibroblast cells. The first cell or tissue type may be cancerous tissue. The first cell or tissue type may be cancer associated stroma. The first cell or tissue type may be Barrett's tissue. The first cell or tissue type may be Barrett's associated stroma.

In an embodiment, the first cell type is esophageal cancer cell line OE19 and the tissue sample obtained from the patient comprises one or more of esophageal cancer cell line OE21, cancer associated myofibroblast cells and adjacent tissue myofibroblast cells (optionally wherein the sample comprises all of these), wherein the selected plurality of wavelengths of radiation correspond to at least two of the following wavenumbers (cm$^{-1}$) of radiation: 1375, 1381, 1400, 1406, 1418, 1692, 1697.

Alternatively, the first cell type may be esophageal cancer cell line OE21 and the tissue sample obtained from the patient comprises one or more of esophageal cancer cell line OE19, cancer associated myofibroblast cells and adjacent tissue myofibroblast cells (optionally wherein the sample comprises all of these), wherein the selected plurality of wavelengths of radiation correspond to at least two of the following wavenumbers (cm$^{-1}$) of radiation: 1443, 1449, 1466, 1472, 1539, 1545, 1551.

In an embodiment, the first cell type is cancer associated myofibroblast cells and the tissue sample obtained from the patient comprise s one or more of esophageal cancer cell line OE19, esophageal cancer cell line OE21, and adjacent tissue myofibroblast cells (optionally wherein the sample comprises all of these), wherein the selected plurality of wavelengths of radiation correspond to at least two of the following wavenumbers (cm$^{-1}$) of radiation: 1443, 1508, 1522, 1678, 1684, 1692.

In an embodiment, the first cell type is adjacent tissue myofibroblast cells and the tissue sample obtained from the patient comprises one or more of esophageal cancer cell line OE19, esophageal cancer cell line OE21, and cancer associated myofibroblast cells (optionally wherein the sample comprises all of these), wherein the selected plurality of wavelengths of radiation correspond to at least two of the following wavenumbers (cm$^{-1}$) of radiation: 1049, 1103, 1146, 1200, 1206, 1400, 1424, 1466, 1472.

In an embodiment, the first tissue type is esophageal cancerous tissue and the tissue sample obtained from the patient comprises one or more of cancer associated stroma, Barrett's tissue and Barrett's associated stroma (optionally wherein the sample comprises all of these), wherein the selected plurality of wavelengths of radiation correspond to at least two of the following wavenumbers (cm$^{-1}$) of radiation: 1460, 1466, 1472, 1480, 1485.

In an embodiment, the first tissue type is cancer associated stroma and the tissue sample obtained from the patient comprises one or more of esophageal cancerous tissue, Barrett's tissue and Barrett's associated stroma (optionally wherein the sample comprises all of these), wherein the selected plurality of wavelengths of radiation correspond to at least two of the following wavenumbers (cm$^{-1}$) of radiation: 999, 1007, 1018, 1061, 1067, 1073.

In an embodiment, the first tissue type is Barrett's tissue and the tissue sample obtained from the patient comprises one or more of esophageal cancerous tissue, cancer associated stroma and Barrett's associated stroma (optionally wherein the sample comprises all of these), wherein the selected plurality of wavelengths of radiation correspond to at least two of the following wavenumbers (cm$^{-1}$) of radiation: 1375, 1406, 1412, 1418, 1443, 1449, 1466.

The first tissue type may be Barrett's associated stroma and the tissue sample obtained from the patient comprises one or more of esophageal cancerous tissue, cancer associated stroma, and Barrett's tissue (optionally wherein the sample comprises all of these), wherein the selected plurality of wavelengths of radiation correspond to at least two of the following wavenumbers (cm$^{-1}$) of radiation: 1375, 1406, 1412, 1418, 1443, 1449, 1466.

According to a fifth aspect there is provided a computer program comprising computer readable instructions configured to cause a computer to carry out a method according to the first aspect or any of its associated options.

According to a sixth aspect there is provided a computer readable medium carrying a computer program according to the fifth aspect of the invention. According to a seventh aspect there is provided a computer apparatus for selecting wavelengths of radiation for use in radiation absorption spectroscopy that discriminate between different cell or tissue types, the computer apparatus comprising a memory storing processor readable instructions, and a processor arranged to read and execute instructions stored in said memory, wherein said processor readable instructions comprise instructions arranged to control the computer to carry out a method according to the first aspect or any of its associated options.

The first cell type and the second cell type may be selected from any two of the following cell lines: esophageal cancer OE19, OE21, cancer associated myofibroblast (CAM) and adjacent tissue myofibroblast (ATM).

The first tissue type and the second tissue type may be selected from any two of the following: cancerous tissue, cancer associated stroma (CAS), Barrett's tissue and Barrett's associated stroma (BAS) esophageal cancer tissue.

As described herein, the patient may be any suitable patient but is typically a mammal, preferably a human. The patient may already have been diagnosed with a given condition (e.g. the identified disease) or may not have been diagnosed with a respective condition to be determined.

Embodiments will now be described by way of example only, with reference to the accompanying figures, in which.

Figure 3A:
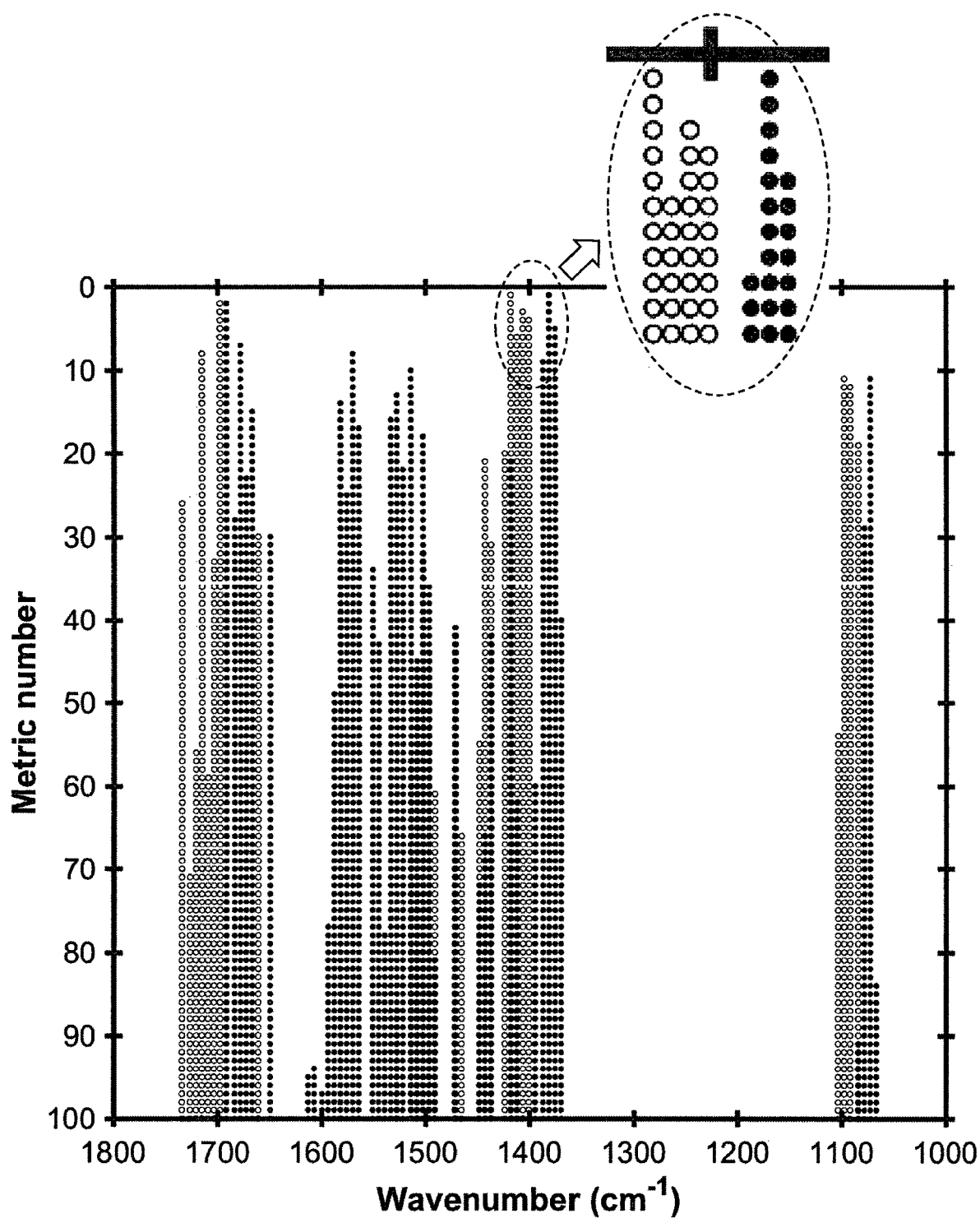
Figure 3B:
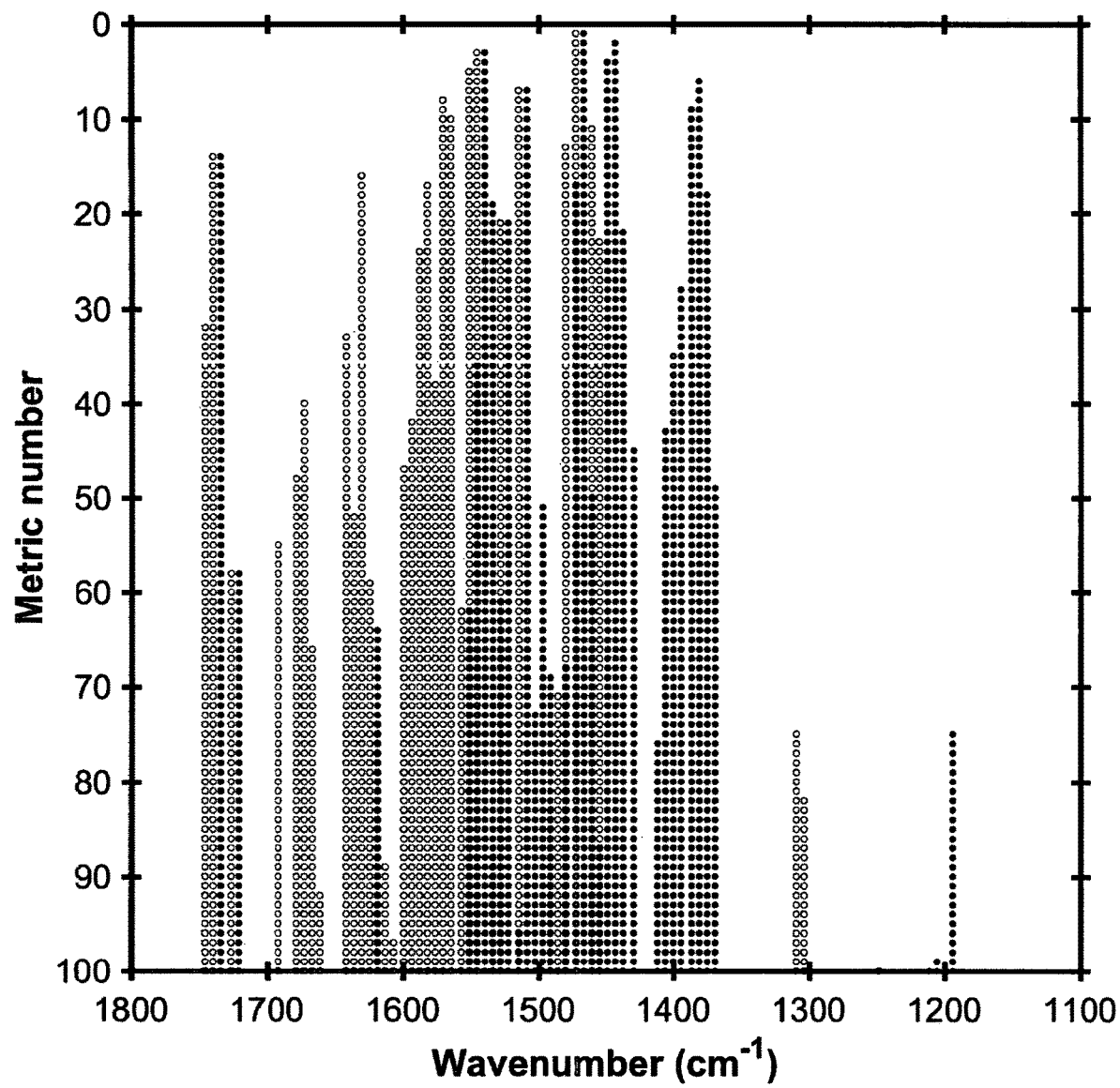
Figure 3C:
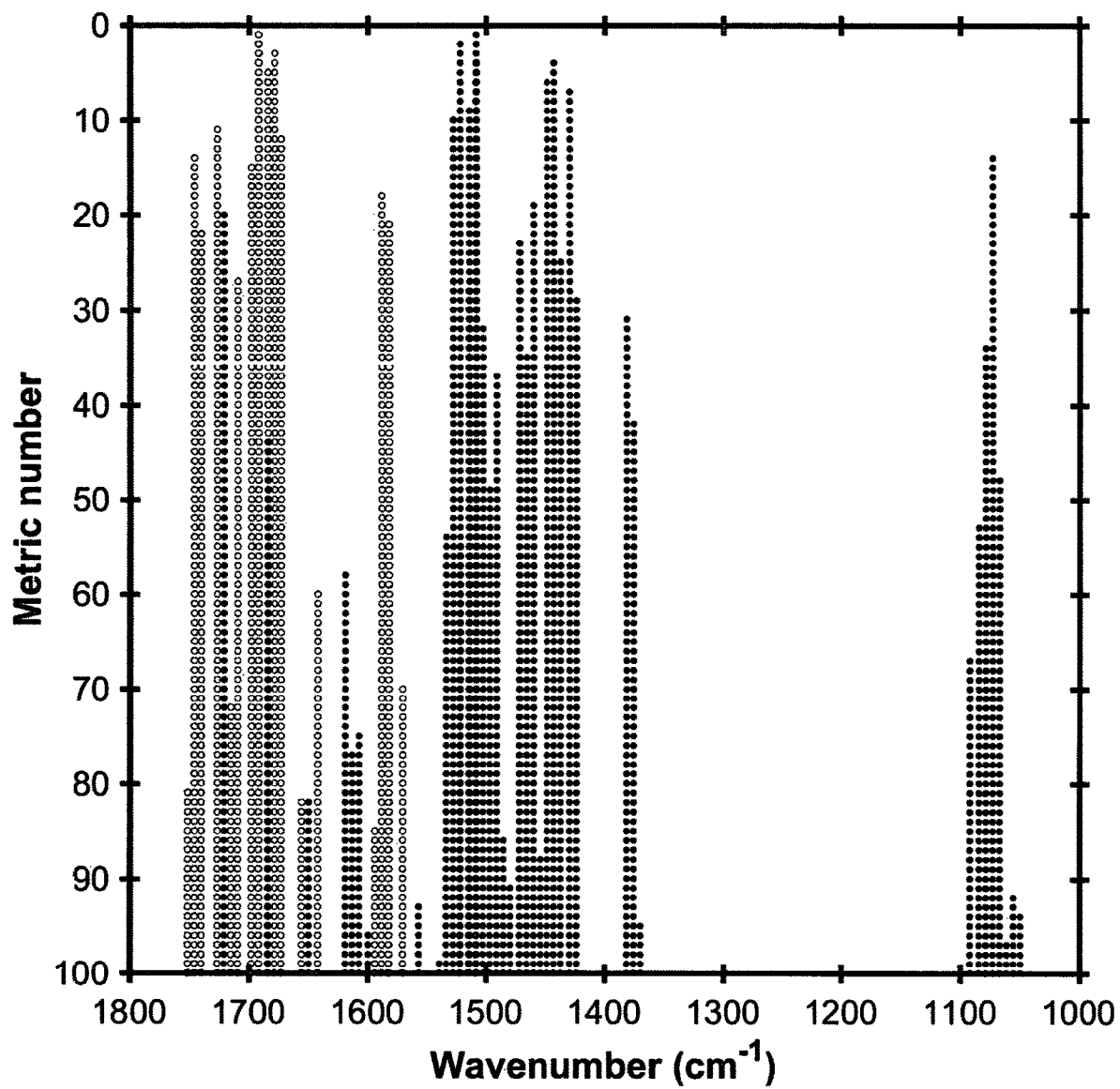
Figure 3D:
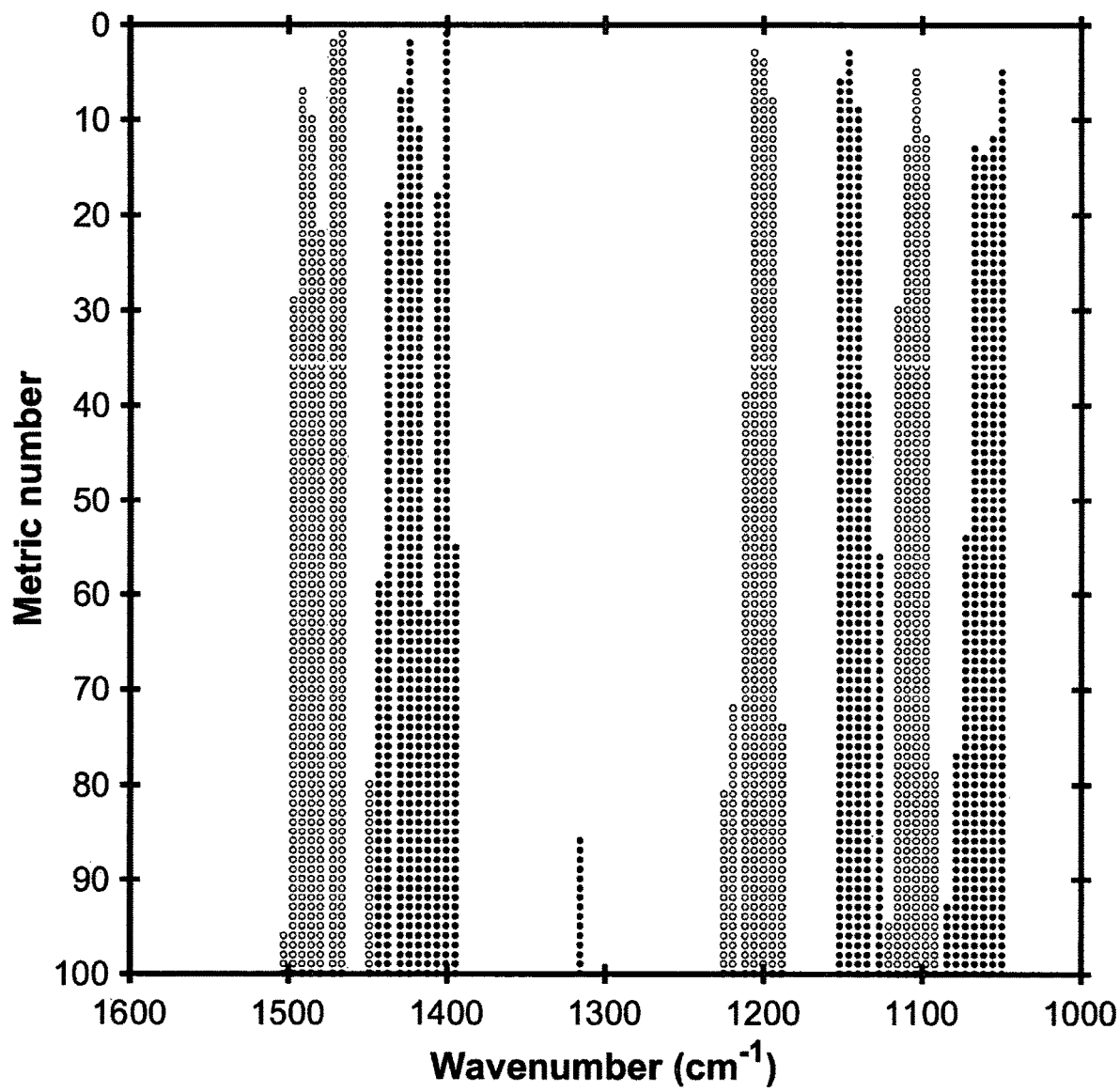
Figure 4:
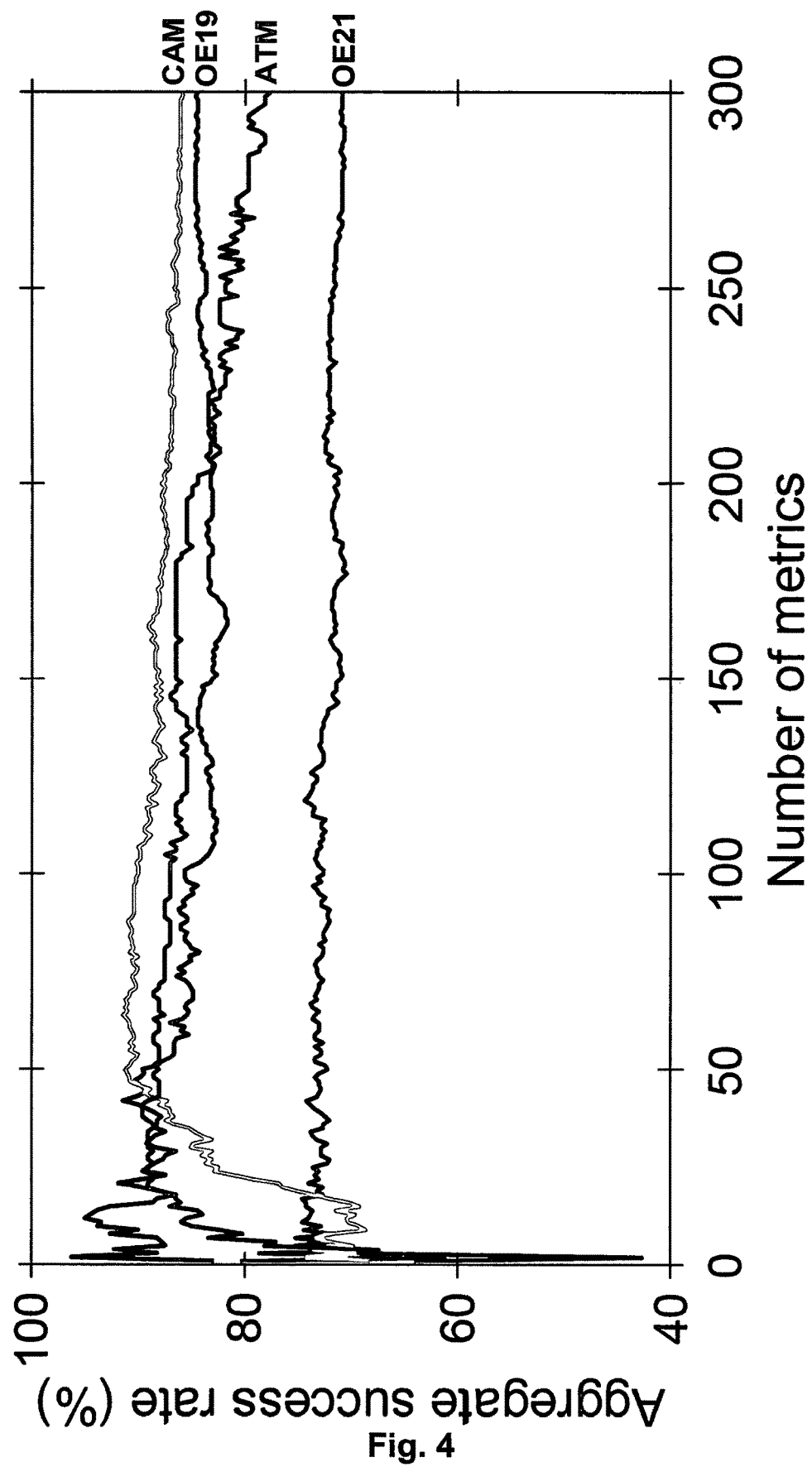
Figure 5:
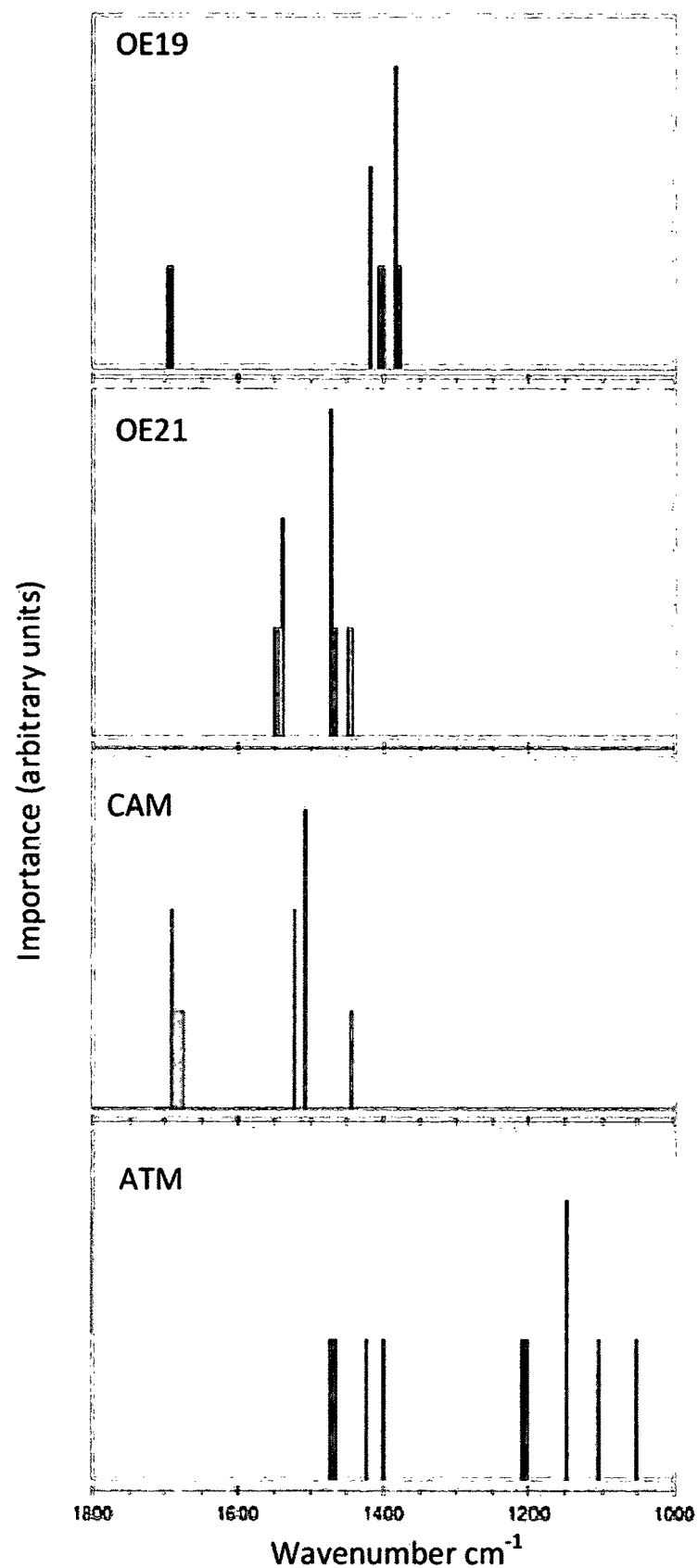
Figure 6:
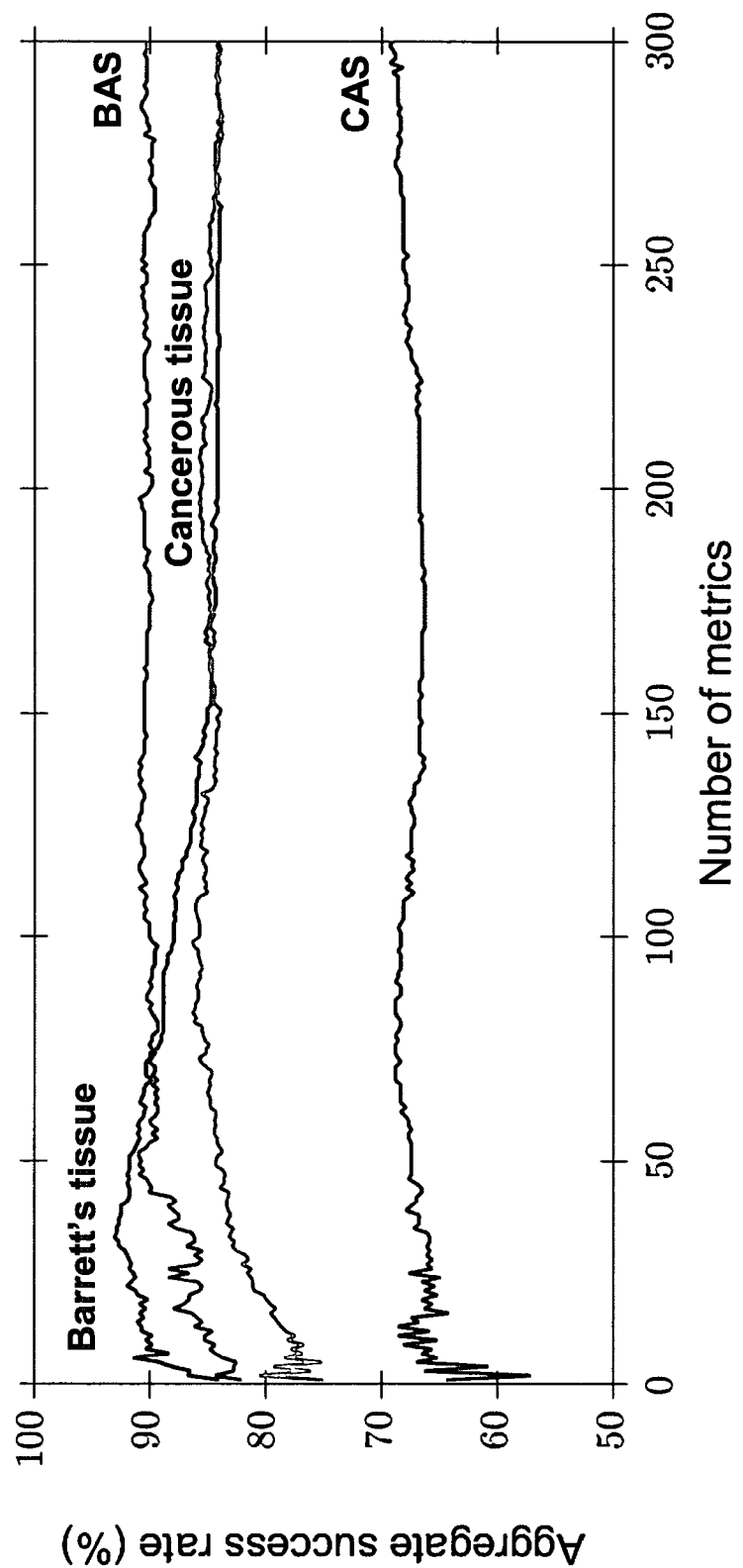
Figure 7:
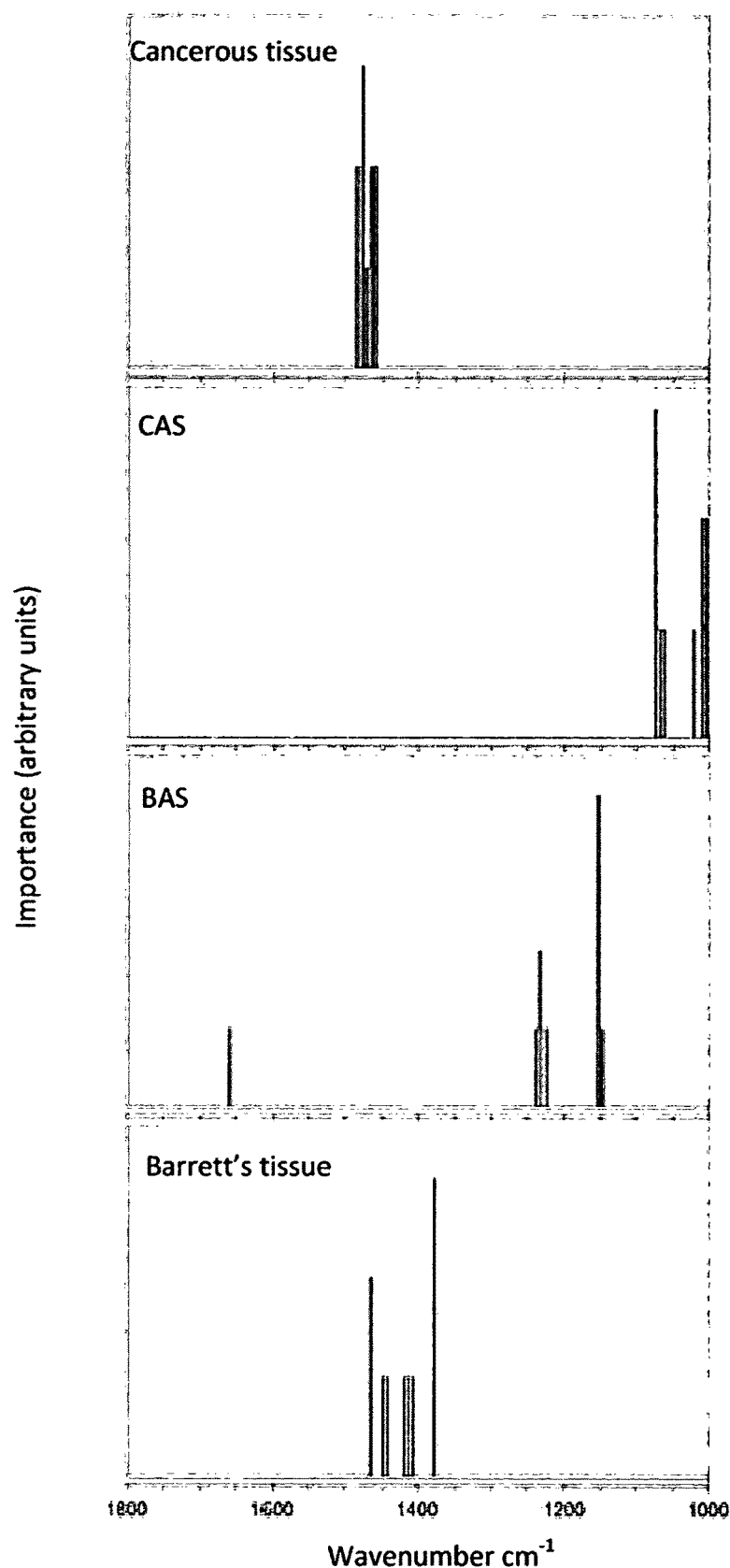
Figure 8A:
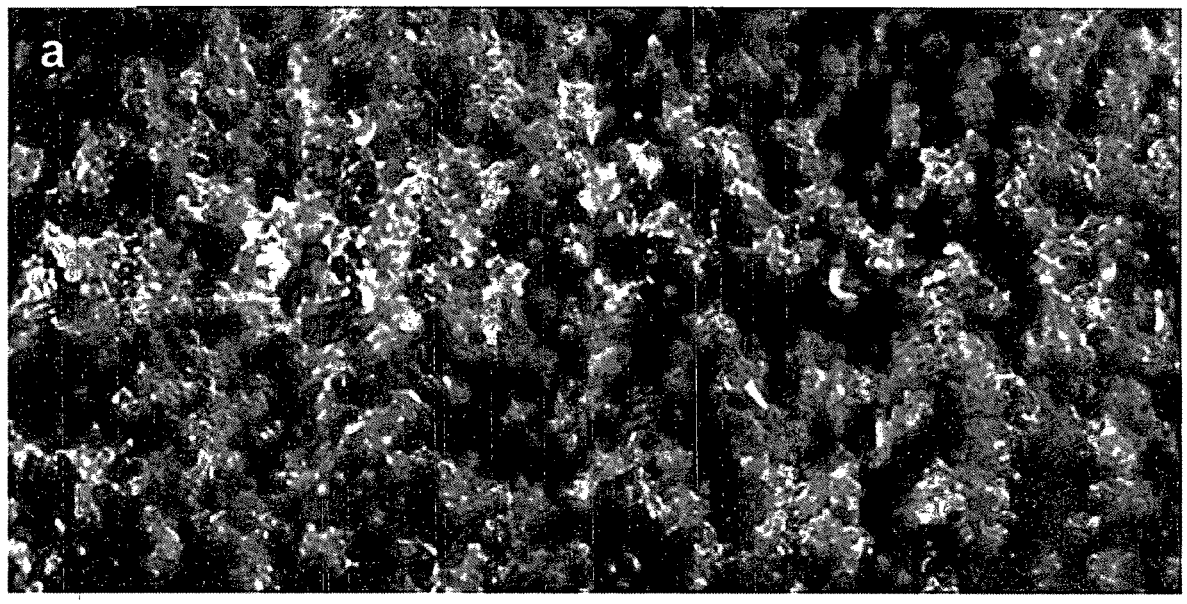
Figure 8B:
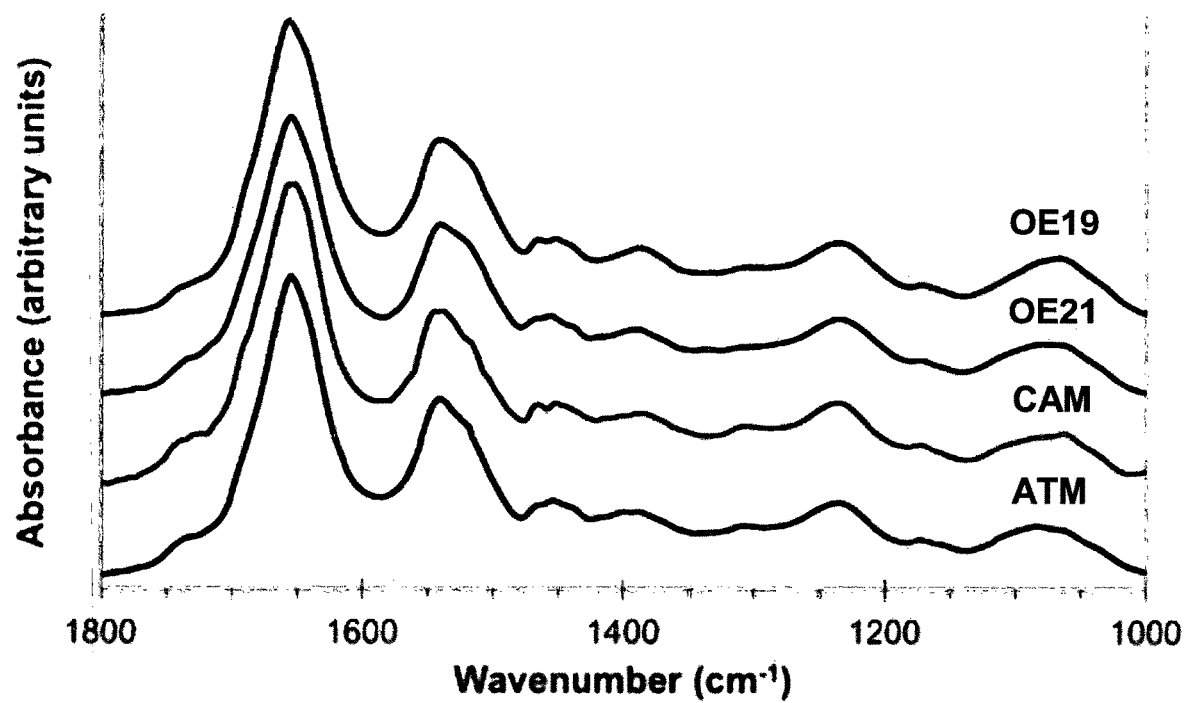
Figure 9:
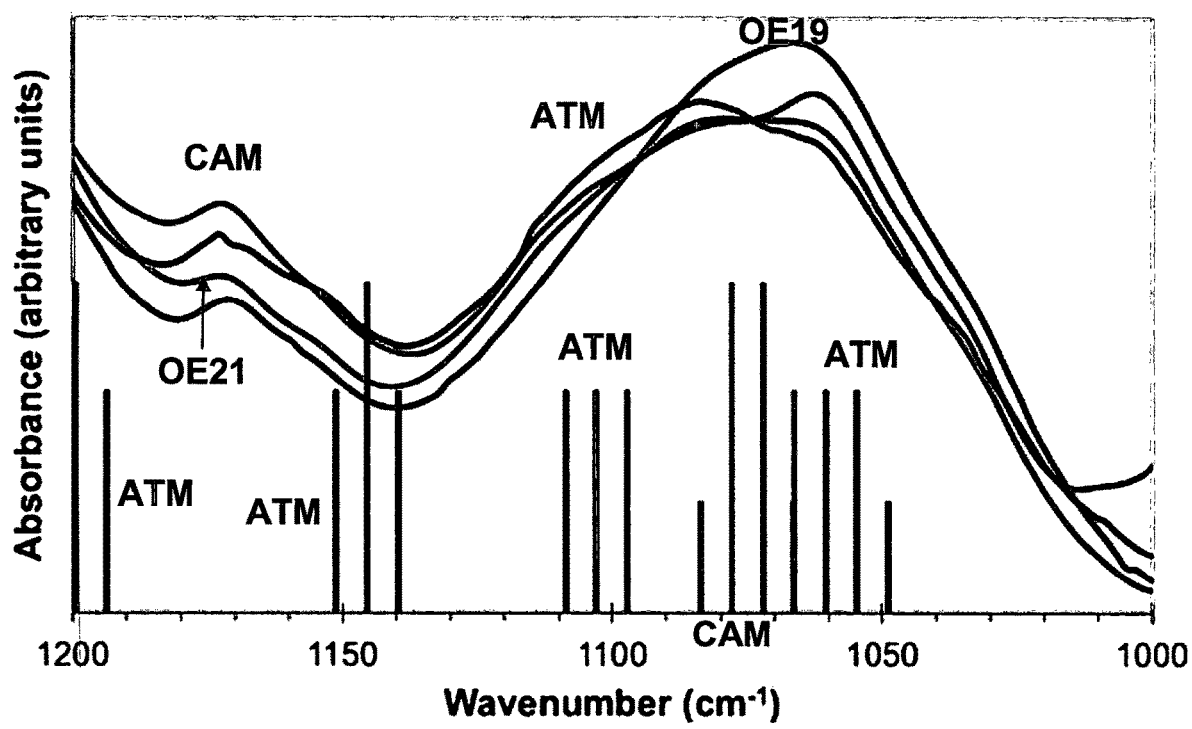
Figure 10A:
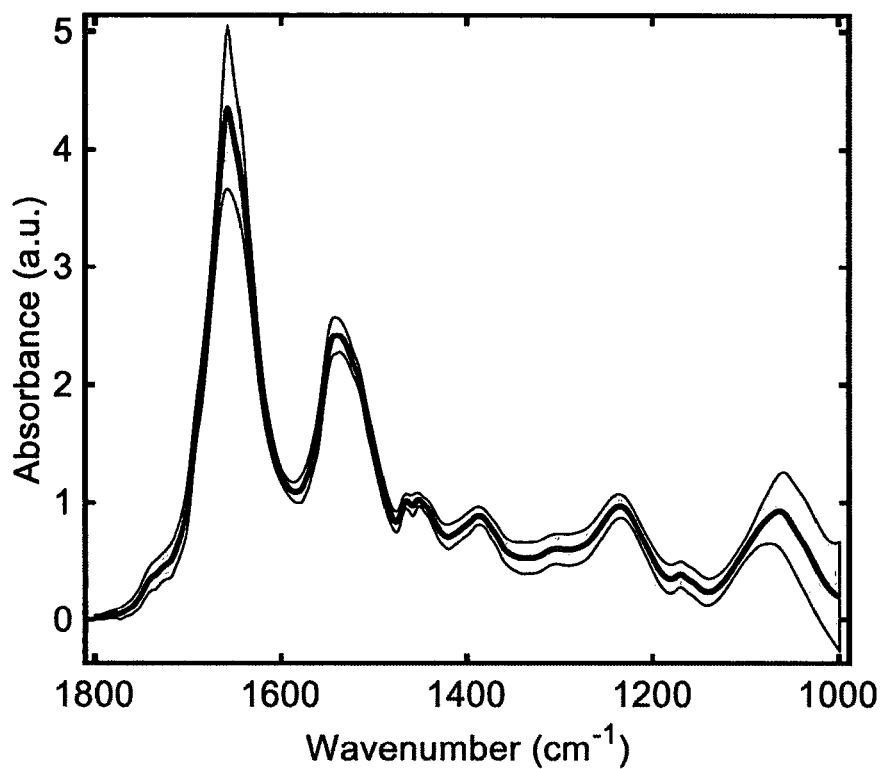
Figure 10B:
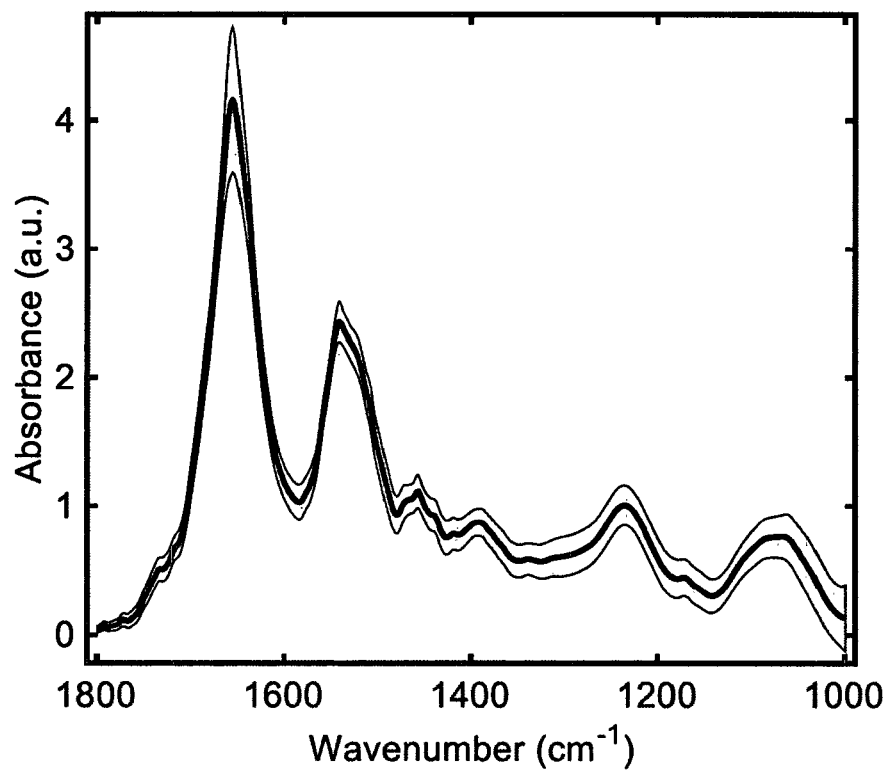
Figure 10C:
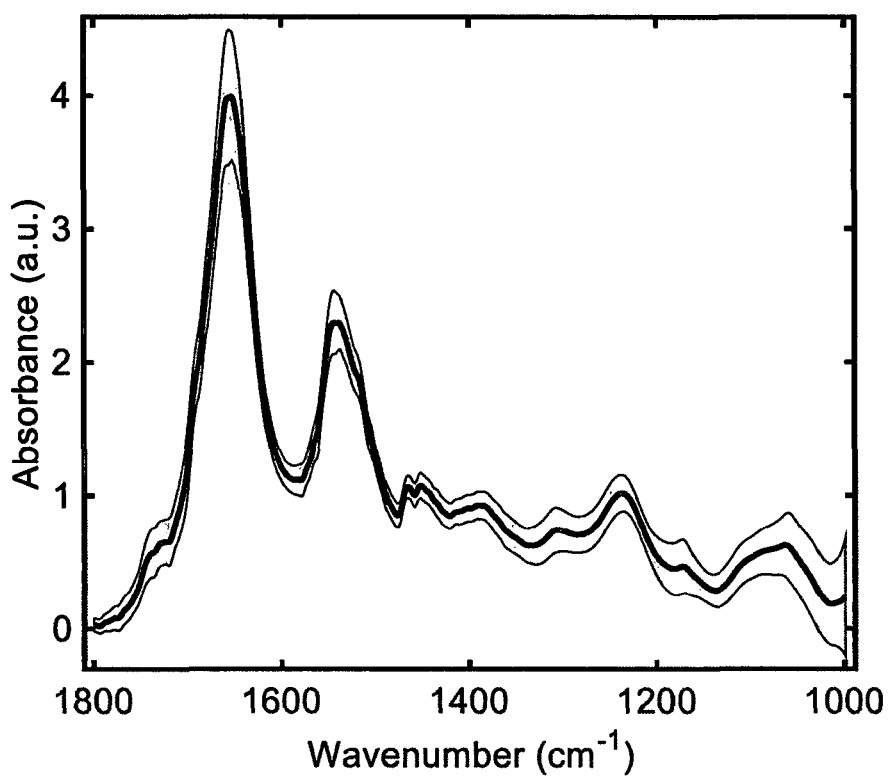
Figure 10D:
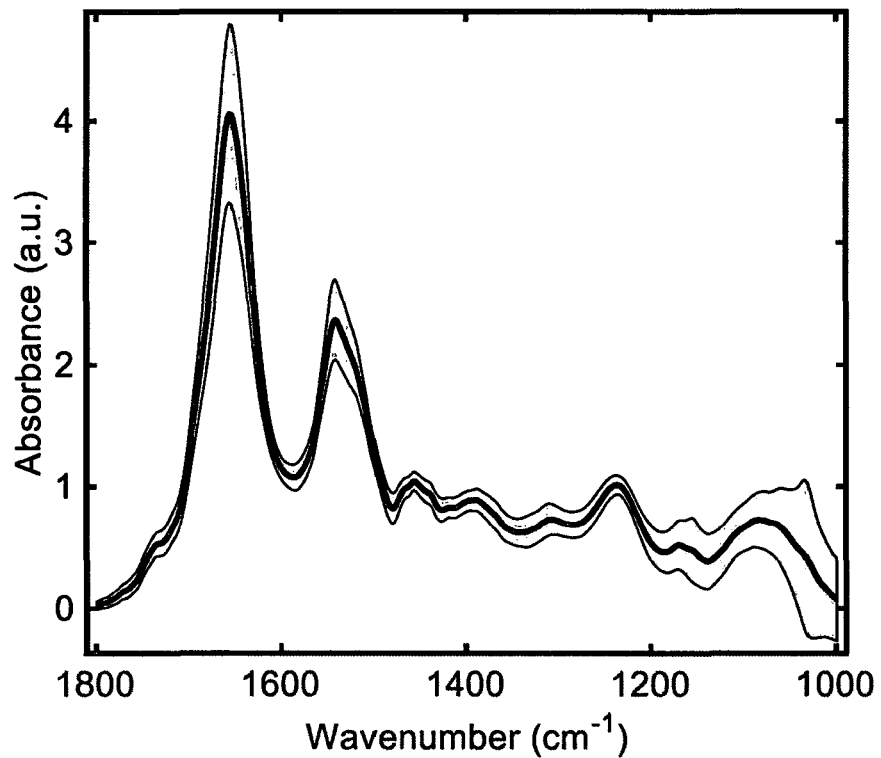

FIG. 2, consisting of FIGS. 2A-2D, shows graphs of the relative scores for each metric as plotted against the wavenumbers that make up each metric, as scored by a method according to an embodiment of the invention;

FIG. 3, consisting of FIGS. 3A-3D, shows graphs of the one hundred best-scoring metrics, as scored by a method according to an embodiment of the invention, for four different cell types;

FIG. 4 shows a graph of the aggregate success rates, as calculated via a method according to an embodiment of the invention, for the four cell types discussed in relation to FIG. 2 and FIG. 3;

FIG. 5 shows four graphs of the relative importance of the wavelengths belonging to the five top-scoring metrics for the four cells of FIGS. 2-4;

FIG. 6 shows a graph of the aggregate success rates, as calculated via a method according to an embodiment of the invention, for four different tissue types;

FIG. 7 shows four graphs of the relative importance of the wavelengths belonging to the five top-scoring metrics, as scored by a method according to an embodiment of the invention, for the four cells of FIG. 6;

FIG. 8A shows a FTIR image of OE19 cells (~5000) integrated over all wavelengths; and FIG. 8B shows the average FTIR spectra over all pixels for OE19 (green line), OE21 (red line), CAM (purple line) and ATM (blue line);

FIG. 9 shows a comparison of Spectral Profiles. The average spectra for the (a) OE19 (green line), (b) OE21 (red line) CAM (purple line) and (d) ATM (blue line) in the region 1000-1200 cm$^{-1}$. The histograms show the wavenumbers that are found to be important in discriminating between the CAM (purple) and ATM (blue) cells for the optimum number of metrics; and FIG. 10, consisting of FIGS. 10A-10D, shows Spectral Standard Deviations for average spectra with standard deviation for OE19 (FIG. 10A), OE21 (FIG. 10B), CAM (FIG. 10C) and ATM (FIG. 10D).

Fourier transform infrared spectroscopy (FTIR) involves illuminating a sample with a range of wavelengths of radiation and measuring how well the sample absorbs each wavelength of radiation. Different chemical bonds in the sample absorb different wavelengths of radiation by different amounts. Biological samples typically contain a large variety of different chemical bonds. The invention allows discrimination of different biological cell types or tissue types by analysing differences between how the different cell types or tissue types absorb radiation at different wavelengths. FTIR typically yields information relating to the radiation absorption behaviour of the sample across several thousand wavelengths. An FTIR measurement of a biological sample may, for example, output a two-dimensional image of the sample, with each pixel of the image comprising an absorption spectrum containing information on the many excitation modes of the large number of different chemical bonds contained in the biological sample.

Figure 1A:
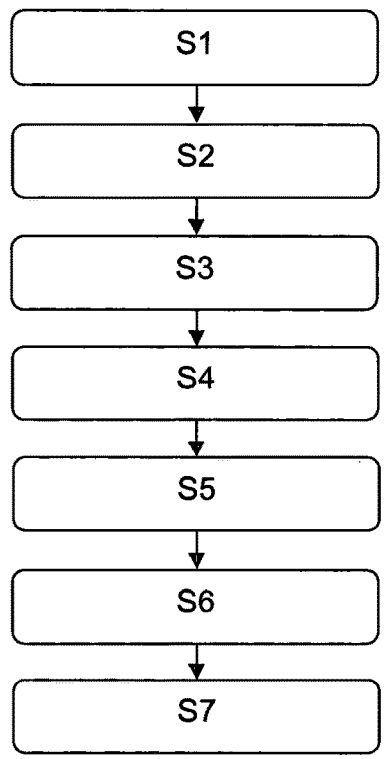
FIG. 1A shows a flowchart of a method of selecting wavelengths of radiation capable of discriminating a first cell or tissue type from a different cell or tissue type for use in radiation absorption spectroscopy according to an embodiment of the invention.

FIG. 1A shows a flowchart of a method of selecting wavelengths of radiation capable of discriminating a first cell or tissue type from a different cell or tissue type for use in radiation absorption spectroscopy according to an embodiment of the invention. Briefly, the method comprises steps of: at S1, obtaining absorption spectra; at S2, defining a set of metrics; at S3, performing a mathematical function on the metrics; at S4, generating distributions of the metrics; at S5, determining an extent of similarity between the distributions; at S6, ranking the metrics based on the extent of similarity between the distributions; and at S7, selecting wavelengths associated with higher ranked metrics.

The first step S1 in the method of FIG. 1A includes obtaining absorption spectra. A first set of absorption spectra is obtained for the first cell or tissue type and a second set of absorption spectra is obtained for the different cell or tissue type. The first set of absorption spectra comprises an absorption spectrum obtained at each spatial region of a plurality of different spatial regions of the first cell or tissue type. The second set of absorption spectra comprises an absorption spectrum obtained at each spatial region of a plurality of different spatial regions of the different cell or tissue type.

The spatial regions may, for example, be pixels of an image of the first cell or tissue type or the different cell or tissue type. For example, the first step S1 may comprise acquiring what may be referred to as an FTIR data cube for each of the first cell or tissue type and the different cell or tissue type. An FTIR data cube may comprise an image of one of the cell or tissue types. The image may comprise a first number (i) of pixels along a first dimension of the data cube and a second number (j) of pixels along a second dimension of the data cube, the first dimension being orthogonal to the second dimension. For example, the total size of the image (i×j) may comprise up to about 5000 pixels, e.g. about 5000 pixels. The third dimension of the data cube is orthogonal to both the first dimension and the second dimension. The third dimension comprises an FTIR spectrum at each pixel of the image, the FTIR spectrum having k data points. For example, the third dimension may comprise absorption spectra across a range of wavelengths from about 900 cm$^{-1}$ to about 4000 cm$^{-1}$. The data points k of the absorption spectra may occur at interval steps across the range of wavelengths, e.g. about 2 cm$^{-1}$ steps. Each absorption spectrum may be corrected for Mie scattering effects. The FTIR data cube may be understood as being an image of a cell or tissue type comprising i×j pixels, whereby each pixel is an absorption spectrum of the cell or tissue type, the absorption spectrum having k data points.

The second step S2 in the method shown in FIG. 1A includes defining a set of metrics. A set of metrics is defined for each spatial region of the first cell or tissue type belonging to the first set of absorption spectra. A corresponding set of metrics is defined for each spatial region of the different cell or tissue type belonging to the second set of absorption spectra. Each metric comprises at least two numerical entries that provide information corresponding to the quantities of radiation absorbed for at least two different wavelengths for the given spatial region. That is, each cell or tissue type is parameterized across the absorption spectra via the calculation of metrics that are associated with the amounts of radiation absorbed by the cell or tissue types at different wavelengths of radiation. The metrics in a given set comprise different combinations of wavelengths of radiation. That is, for a metric consisting of two numerical entries, the first numerical entry may be the amount of radiation absorbed at a first wavelength ($A\lambda_1$) and the second numerical entry may be the amount of radiation absorbed at a different wavelength ($A\lambda_2$). The metrics may comprise a greater number of numerical entries, e.g. three numerical entries. The metrics may be defined such that all possible combinations of wavelength pairs within a spectral range are included within a given set of metrics. For example, the metrics may be defined such that all possible wavelength pairs occurring at an interval size of 6 cm$^{-1}$ within the range of from about 1000 cm$^{-1}$ to about 1800 cm$^{-1}$ are included. Other spectral ranges and/or other interval sizes may be used. If the first cell or tissue type is known then the spectral range used may be selected using pre-existing knowledge of the first cell or tissue type's radiation absorption behaviour. That is, the spectral range may be selected such that at least some of the wavelengths used are known to interact with the first cell or tissue type in an identifiable manner.

The third step S3 in the method shown in FIG. 1A includes performing a mathematical function on each metric. The first mathematical function acts on the at least two entries of each metric so as to generate a characteristic value for each metric. That is, the outcome of the first mathematical function is a characteristic value that can be associated with that particular metric. The outcome of the first mathematical function (i.e. the characteristic value) is dependent on the amount of radiation absorbed at each of the at least two different wavelengths belonging to the metric. For example, a given metric for a given spatial region of the first cell or tissue type may comprise the amount of radiation absorbed at a wavelength of 1750 cm$^{-1}$ (e.g. X) and the amount of radiation absorbed at a wavelength of 1100 cm$^{-1}$ (e.g. Y). The first mathematical function acts on X and Y to produce an outcome that is dependent on both X and Y. The outcome is assigned to that metric as a characteristic value of the metric.

The first mathematical function may, for example, determine a ratio between the amounts of radiation absorbed at the at least two different wavelengths of a metric. Determining a ratio between the amounts of radiation absorbed at the at least two different wavelengths of a metric advantageously negates absorption spectra measurement variables such as, for example, thicknesses of the samples of the first cell or tissue type and the different cell or tissue type from which the first and second absorption spectra were obtained. The first mathematical function may determine something other than a ratio. For example, the first mathematical function may determine a difference between the amounts of radiation absorbed at the at least two different wavelengths of a given metric.

Defining the metrics such that many or all of the possible pairs of wavelengths are accounted for means that the method of FIG. 1A treats all absorption spectra data equally. That is, no biological significance is attributed at any particular wavelength of radiation. From this start of no assumed importance, the method is able to demonstrate the existence of biomarkers (i.e. distinct fingerprints) that can be used to discriminate between the first cell or tissue type and the different cell or tissue type using wavelengths of radiation that have not been identified using known methods. The fourth step S4 in the method of FIG. 1A includes generating distributions for the metrics. A distribution comprising the outcomes of the first mathematical function for every spatial region of a given cell type or tissue type is generated for each metric. That is, a given metric (i.e. a given combination of absorption information at different wavelengths of radiation) is present for each of the plurality of different spatial regions of a given cell or tissue type. The characteristic value for a given metric may vary between the different spatial regions of a given cell or tissue type. Thus each metric may have its own distribution of outcomes of the first mathematical function. The characteristic value may vary between different spatial regions of a given cell or tissue type due to, for example, structural differences and/or differences in molecular composition of the cell or tissue type across different regions of the cell or tissue type. Each distribution comprises the outcomes of the first mathematical function across the plurality of different spatial regions belonging to a given cell or tissue type for a given metric. The distributions may, for example, be histograms. Each histogram may be accurately described and analysed by treating them as a Gaussian distribution.

The fifth step S5 in the method of FIG. 1A includes determining an extent of similarity between the distributions. The distribution for a given metric belonging to the first cell or tissue type is compared with the distribution of the corresponding metric belonging to the different cell or tissue type. An extent of similarity between the distributions is determined.

Figure 1B:
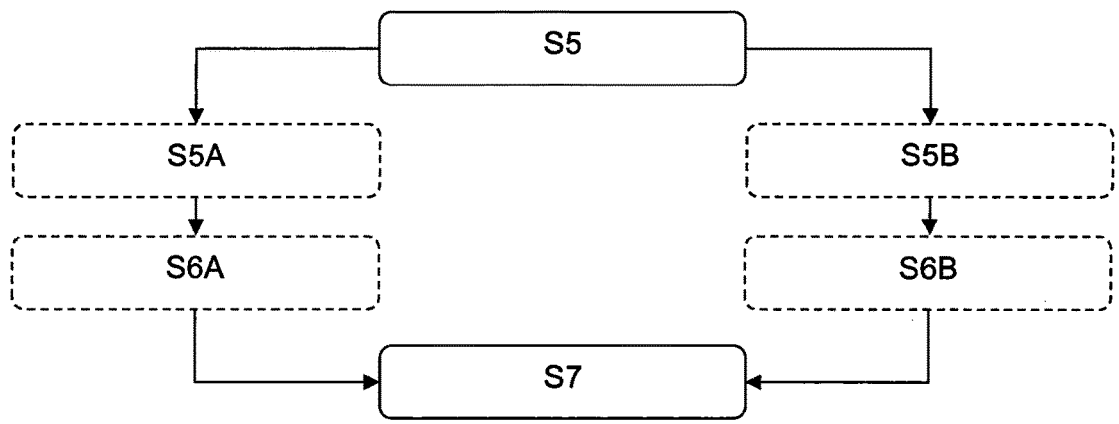
FIG. 1B shows a flow chart of alternative methods of determining an extent of similarity between distributions according to an embodiment of the invention.

Determining the extent of similarity between the distributions may be achieved in a plurality of different ways. FIG. 1B shows a flowchart of alternative methods of determining an extent of similarity between the distributions according to an embodiment of the invention. As can be seen from FIG. 1B, the fifth step S5 of the method of FIG. 1A may be carried out in a plurality of different ways. For example, a first method includes a first sub-step S5A of determining an area of overlap between the distributions. The total area of the distributions may be compared to an area of overlap between the distributions. Distributions having a greater area of overlap may be considered as being more similar than distributions having a smaller area of overlap.

Alternatively, a second method includes a first sub-step S5B of treating the distributions as probability distribution functions. That is, the distributions may be mathematically treated as being probability distribution functions and the extent of similarity between the probability distribution functions may be determined by comparing parameters of the probability distribution functions. The parameters of the probability distribution functions may, for example, comprise a mean value and/or a standard deviation of the probability distribution functions. Probability distributions having distinctive parameters may be considered as being less similar than probability distribution functions having like parameters.

As another alternative, the distributions may be approximated as being Gaussian distributions and the parameters of the Gaussian distributions may be compared with each other to determine the extent of similarity between the distributions. The fifth step S5 is repeated for each of the metrics such that the extent of similarity between the first cell or tissue type and the different cell or tissue type is known for every metric. The metrics may then be ranked by quantifying the extent of similarity between the probability distribution functions.

Referring again to FIG. 1A, the sixth step S6 in the method includes ranking the metrics based on the extent of similarity between the distributions belonging to the metrics. The metrics are ranked such that metrics associated with distributions having a lesser extent of similarity rank higher than distributions having a greater extent of similarity. That is, metrics that generate distinctive distributions rank higher than metrics that generate like distributions. Ranking the metrics may be achieved in a number of ways. For example, when comparing the total area of the distributions to an area of overlap between the distributions (such as in the first sub-step S5A shown in FIG. 1B), the following equation may be used to rank the metrics:

$$Ranking = \frac{1 - \text{Area of overlap between the distributions}}{\text{Total area of the distributions}}$$

Referring to FIG. 1B, a second sub-step S6A of the first method shown in FIG. 1B includes ranking the metrics according to the area of overlap between the distributions. The greater the area of overlap between two given distributions, the more similar those distributions are. Thus, the lower the ranking is for the metric that is associated with those two distributions. On the other hand, the smaller the area of overlap between two given distributions, the less similar those distributions are. Thus, the higher the ranking is for the metric that is associated with those two distributions.

As discussed above, an alternative method of ranking the metrics includes mathematically treating the distributions as probability distribution functions and ranking probability distributions functions having distinctive parameters of the probability distribution functions. A second sub-step S6B of the second method shown in FIG. 1B includes ranking the metrics using the parameters of the probability distribution functions. The parameters of the probability distribution functions may, for example, comprise a mean value and/or a standard deviation of the probability distribution functions. Said parameters may be used to determine an extent of similarity between the probability distribution functions. Said parameters may be used to determine a probability with which a given outcome belongs to one probability distribution function rather than another probability distribution function. This is discussed in greater detail below with reference to FIG. 1C.

The distributions may be approximated as being Gaussian distributions and the metrics associated with Gaussian distributions having distinctive parameters may be ranked higher than metrics that are associated with Gaussian distributions having similar parameters. The parameters of the Gaussian distributions may, for example, comprise a mean value and/or a standard deviation of the Gaussian distributions. Said parameters may be used to determine an extent of similarity between the approximated Gaussian distributions. For example, said parameters may be used to determine an area of overlap between the Gaussian distributions. Alternatively, the Gaussian distributions may be treated as probability distribution functions, and the parameters of the probability distribution functions may be used to determine an extent of similarity between the probability distribution functions.

Referring again to FIG. 1A, the seventh step S7 in the method includes selecting wavelengths of radiation that are associated with the higher ranked metrics. As discussed above, the metrics are ranked in accordance with how distinct their associated distributions are, with the highest ranked metrics generating the most distinct distributions. The more distinct two distributions are, the greater the difference in absorption behaviour there is between the first cell or tissue type and the different cell or tissue type at the wavelengths of radiation associated with the metric that generated those distributions. Thus, higher ranked metrics comprise wavelengths of radiation which, when used to illuminate the cell or tissue types, result in greater differences in the absorption behaviour of the cell or tissue types. That is, the absorption behaviour of the first cell or tissue type at the wavelengths of radiation associated with the highest ranked metric has the greatest difference to the absorption behaviour of the different cell or tissue type at those wavelengths of radiation when compared to the absorption behaviour at wavelengths of radiation associated with any other metric. The difference in absorption behaviour between the first cell or tissue type and the different cell or tissue type is used to discriminate between the first cell or tissue type and the different cell or tissue type. The higher ranked metrics comprise wavelengths of radiation for use in radiation absorption spectroscopy that are capable of discriminating the first cell or tissue type from the different cell or tissue type.

FIG. 10 shows a flow chart of a method of selecting wavelengths associated with a greater aggregate success rate according to an embodiment. The seventh step S7 may comprise one or more sub-steps S7A-S7E, e.g. all of these additional steps. The sub-steps S7A-S7E may be performed when the identity of the first cell or tissue type is known.

Briefly, the seventh step S7 may comprise one or more sub-steps of: at S7A, defining success rates for the metrics; at S7B, defining mislabelling rates for the metrics; at S7C, scoring the metrics; at S7D, determining aggregate success rates for the combinations of the metrics; and/or at S7E, selecting wavelengths associated with a greater aggregate success rate.

Figure 1C:
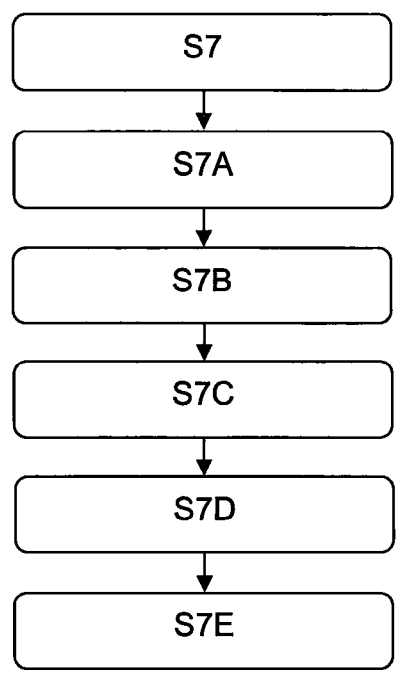
FIG. 1C shows a flow chart of a method of selecting wavelengths associated with a greater aggregate success rate according to an embodiment of the invention.

The first sub-step S7A of the method of FIG. 1C includes defining a success rate for each higher ranked metric. The success rate may be defined for every metric. The success rate is configured to evaluate the frequency by which a given metric correctly identifies whether a given absorption spectrum belongs to the first cell or tissue type and the different cell or tissue type. In order to define the success rate, a first portion of spatial regions belonging to the first cell or tissue type is not used to generate a distribution for each metric. Instead, the first portion of spatial regions is used to test how accurately each metric is able to discriminate between the first cell or tissue type and the different cell or tissue type. The first portion of spatial regions may be smaller than the remaining portion of spatial regions. For example, the first portion of spatial regions may comprise about 25% of the total number of spatial regions whereas the remaining portion of spatial regions comprises about 75% of the total number of spatial regions. Other ratios are however envisaged. The higher ranked metrics are used to allocate each spatial region belonging to the first portion of spatial regions to either the first cell or tissue type or the different cell or tissue type. That is, the higher ranked metrics are used to predict whether each spatial region of the first portion of spatial regions belongs to the first cell or tissue type or the different cell or tissue type. Each metric may be used to predict whether each spatial region of the first portion of spatial regions belongs to the first cell or tissue type or the different cell or tissue type.

A success rate may be defined by performing the first mathematical function on a given metric for each of the spatial regions belonging to the first portion of spatial regions of the first cell or tissue type in order to produce a test outcome. The test outcome is compared with the corresponding distributions (i.e. the distributions associated with the given metric) belonging to the first cell or tissue type and the different cell or tissue type. The comparison is used to predict whether the test outcome belongs to either the first cell or tissue type or the different cell or tissue type. Because the identity of the first cell or tissue type is known, the prediction made by the test outcome may be verified and a success rate for the given metric may be defined as how often the prediction is correct. In general, defining the success rate includes determining the number of spatial regions of the first portion that were correctly allocated using the higher ranking metrics. A success rate may be calculated for any metric. For example, the success rate may be calculated for each metric. The success rate may be calculated for at least the higher ranked metrics. Defining a success rate for the metrics advantageously evaluates how well the metrics can discriminate the cell or tissue types. The success rate demonstrates how accurate the selected wavelengths of radiation are at discriminating the cell or tissue types.

If the distributions are mathematically treated as probability density functions then the test outcomes for a plurality of spatial regions belonging to the first portion of spatial regions of the first cell or tissue type may be used to extract, from the probability density functions, the probability of each of the first portion of spatial regions belonging to the first cell or tissue type. The spatial regions are then predicted to belong to whichever cell or tissue type has the highest associated probability. The predictions may then be verified because the identity of the first cell or tissue type is known, and a success rate for a given metric may be calculated as the frequency with which the given metric correctly predicted the identity of the first portion of spatial regions. The extracted probability of a spatial region belonging to one of the cell or tissue types may be referred to as a confidence value for that cell or tissue type.

The second sub-step S7B of the method of FIG. 1C includes defining a mislabelling rate for the metrics. The mislabelling rate may be determined for every metric. The mislabelling rate may be determined for at least the higher ranking metrics. The mislabelling rate represents the probability that a metric incorrectly identified the different cell or tissue type as being the first cell or tissue type. The metric is used to predict which cell or tissue type a spatial region belonging to the first cell or tissue type belongs to. The probability of the metric belonging to the first cell or tissue type (i.e. the correct cell or tissue type) which is extracted from the probability density function associated with the metric corresponds to the success rate for that metric. The metric is then used to predict which cell or tissue type a spatial region belonging to the different cell or tissue type belongs to. The probability of the metric belonging to the first cell or tissue type (i.e. the incorrect cell or tissue type) which is extracted from the probability density function associated with the metric corresponds to the mislabelling rate for the metric. Defining a mislabelling rate for the metrics advantageously provides further information on which of the associated wavelengths are most accurate for discriminating the first cell or tissue type and the different cell or tissue type.

The third sub-step S7C in the method of FIG. 10 includes scoring the metrics. Each metric may be scored. At least the higher ranking metrics may be scored. The metrics may be scored by performing a second mathematical function on the calculated success rates and mislabelling rates. The metrics may then be scored in accordance with the outcomes of the second mathematical function. The score received by a metric corresponds to the ability of the metric to accurately discriminate between the cell types. The second mathematical function may, for example, be the following equation:

$$score = success\ rate \times (1 - mislabeling\ rate)$$

As previously discussed, the success rate is the rate at which a given cell type is labelled correctly and the mislabelling rate is the rate at which the other cell type(s) are labelled incorrectly as the given cell type.

Figure 2A:
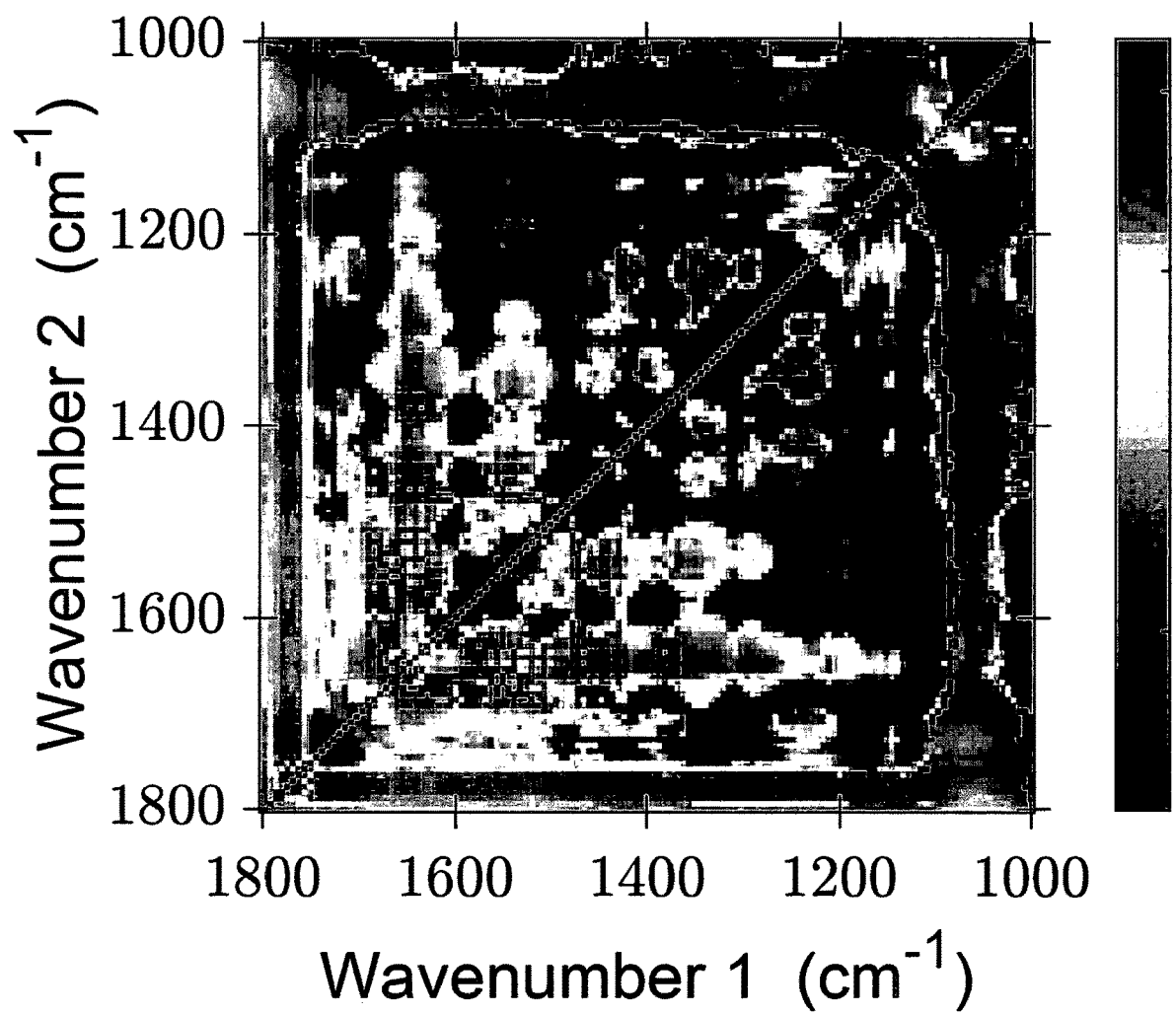
Figure 2B:
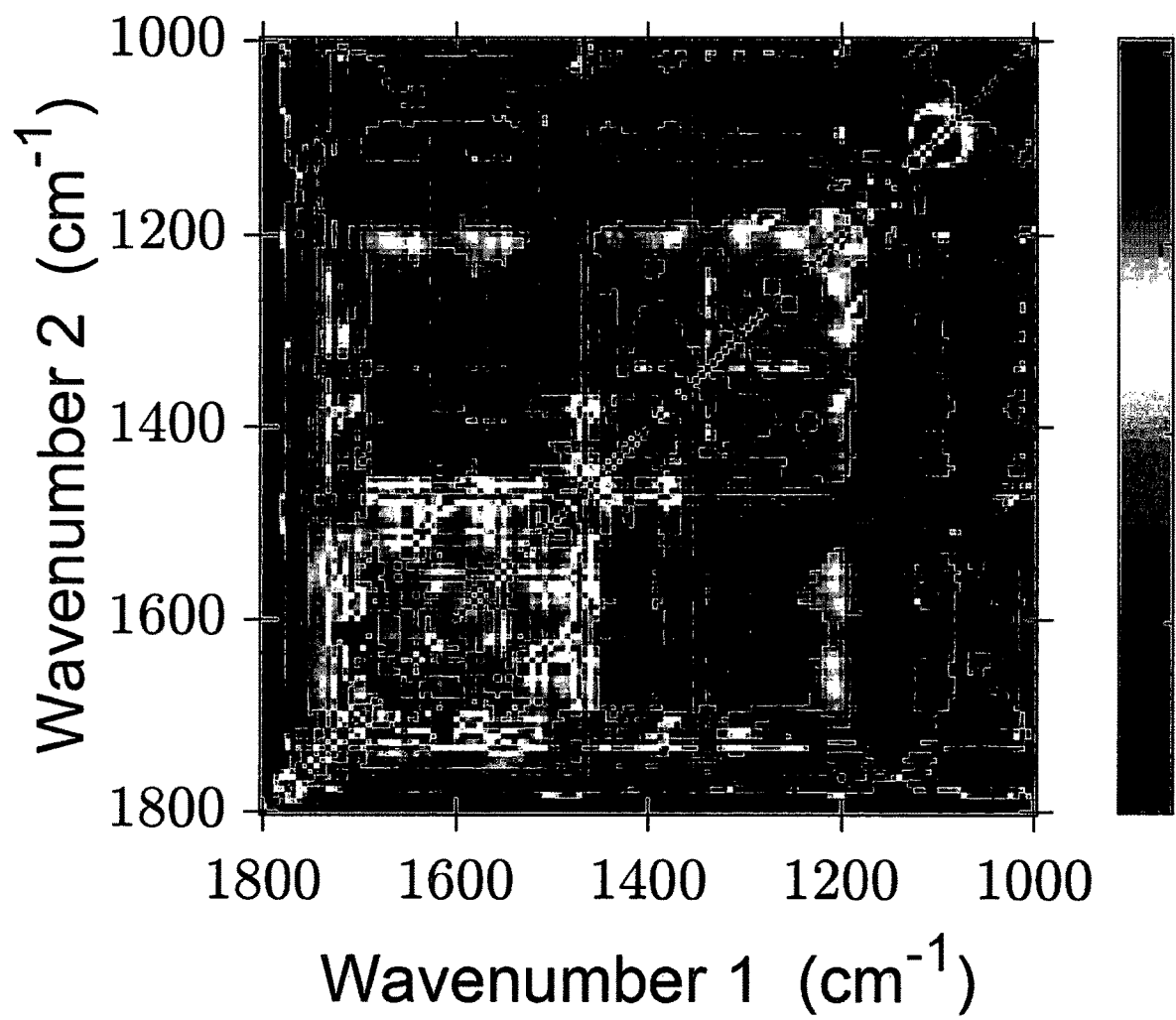
Figure 2C:
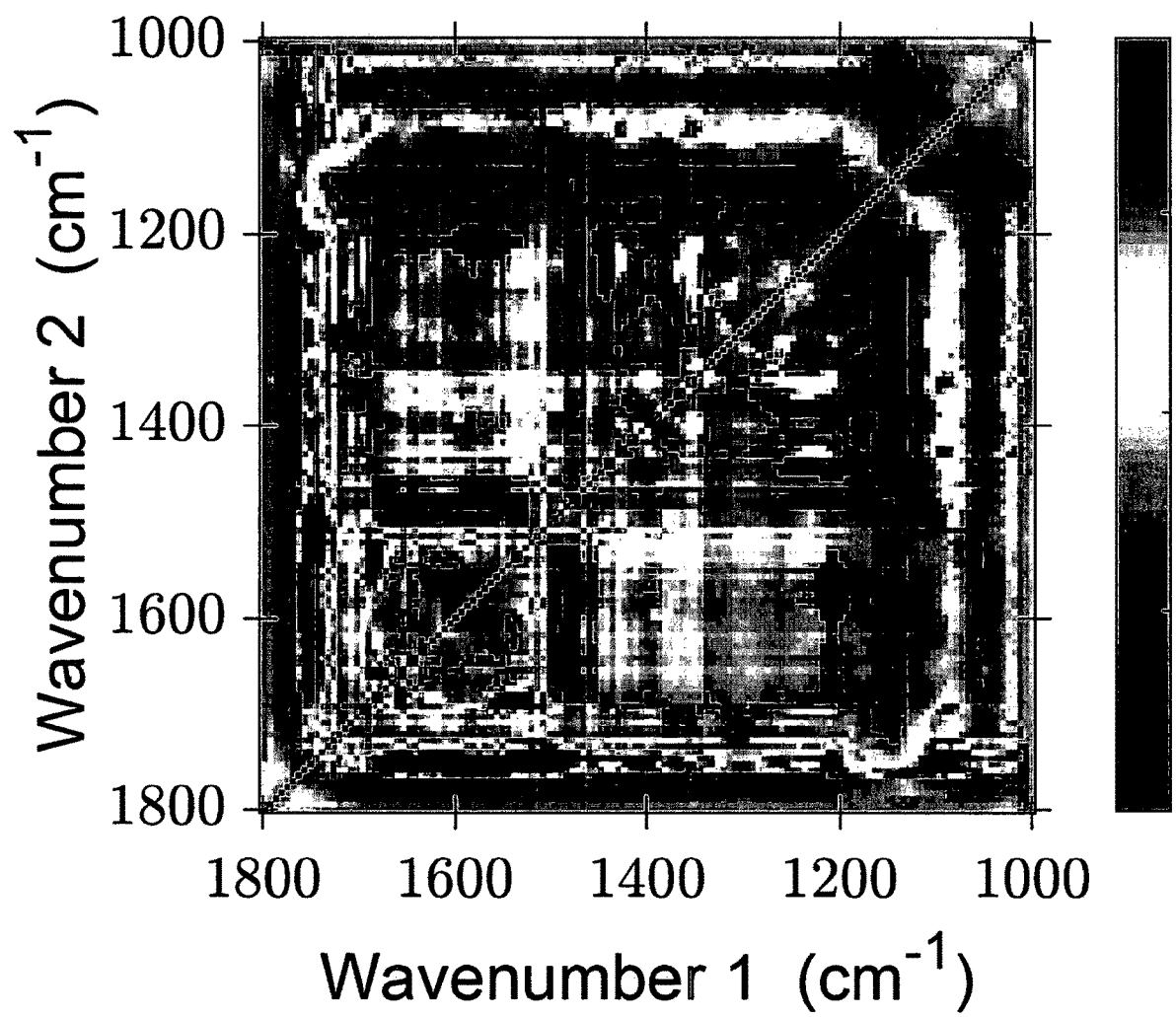
Figure 2D:
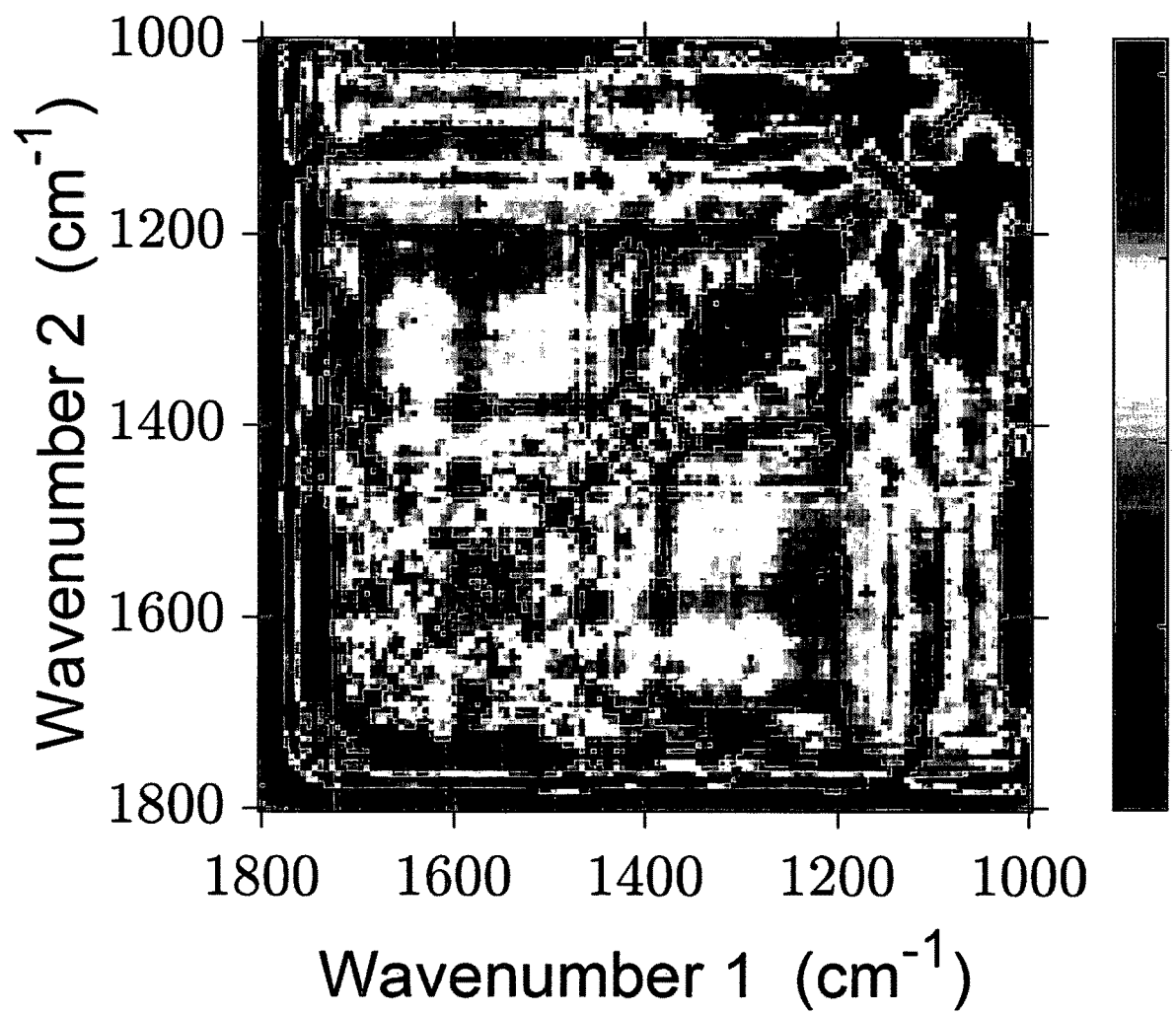

To exemplify the efficacy of the invention, the second mathematical function was performed on four FTIR data cubes. The first FTIR data cube was obtained from an esophageal cancer associated myofibroblast (CAM) cell line. The second FTIR data cube was obtained from an adjacent tissue myofibroblast (ATM) cell line. The third FTIR data cube was obtained from an esophageal cancer OE19 cell line. The fourth FTIR data cube was obtained from an esophageal cancer OE21 cell line. FIG. 2, consisting of FIGS. 2A-2D, shows graphs of the relative scores for each metric as plotted against the wavenumbers that make up each metric. FIG. 2A shows the relative scores of the metrics for the OE19 cell line. FIG. 2B shows the relative scores of the metrics for the OE21 cell line. FIG. 2C shows the relative scores of the metrics for the CAM cell line. FIG. 2D shows the relative scores of the metrics for the ATM cell line. In the example of FIG. 2, red indicates a higher score whereas blue indicates a lower score. As can be seen from FIG. 2, the regions of the spectrums at which each cell type displays unique behaviour (i.e. a low extent of similarity) vary. For the CAM and ATM cell lines, very different behaviour is seen in the graphs of FIG. 2C and FIG. 2D respectively. This highlights the clear discrimination achieved between these two cell types. This is a significant result since Histopathologists find it difficult to distinguish between these cell types using the current standard method of optical microscopy on H&E stained samples. For example, with regard to the CAM cell line (FIG. 2C), high scoring metrics are those that contain at least one high wavenumber around 1750 $cm^{-1}$. The opposite situation is found for ATM (FIG. 2D), where high scoring metrics are often associated with at least one low wavenumber around 1150 $cm^{-1}$.

FIG. 3, consisting of FIGS. 3A-D, shows graphs of the one hundred best-scoring metrics in accordance with the outcomes of the second mathematical function for the CAM, ATM, OE19 and OE21 cell lines. FIG. 3A shows the one hundred best-scoring metrics for the OE19 cell line. FIG. 3B shows the one hundred best-scoring metrics for the OE21 cell line. FIG. 3C shows the one hundred best-scoring metrics for the CAM cell line. FIG. 3D shows the one hundred best-scoring metrics for the ATM cell line. In the example of FIG. 3, each metric consisted of two different wavelengths of radiation. Each metric is therefore represented as two circles (particularly, an unfilled circle and a corresponding filled circle, respectively) on the graphs of FIG. 3, with each circle corresponding to one of the wavenumbers (i.e. the inverse of the wavelength) of the metric. FIG. 3 illustrates the combinations of wavenumbers of radiation that are used as a function of an increasing number of metrics from 1 to 100. FIG. 3A shows a zoomed region of the metrics, showing the unfilled circles and the corresponding filled circles, for clarity. The Manhattan plots of FIG. 3 each show the best 100 metrics. The plots are cumulative, in that the circles (i.e. the unfilled circles and the corresponding filled circles) shown on a horizontal row labelled by metric number N are the circles for the best N metrics. For example, for the best metric (i.e. top metric, metric number N=1), Hence there are two circles, one for each wavenumber for this best metric, at the very top of the plot. For metric number N=2 on the next row down, there are 4 circles, 2 for each metric, for the best 2 metrics (i.e. top 2 metric), since the plots are cumulative. On the third row, there are 6 circles, 2 for each metric, for the best 2 metrics (i.e. top 3 metrics), etc. Thus, wavenumbers shown for metric number N must also be shown for metric number N+1 while at most two additional wavenumbers may be shown for metric number N+1 compared with metric number N. Note that some wavenumbers may be the same from one metric number to the next, and so some circles are overlaid. That is, amongst the top 100 metrics, for example, not all the wavenumbers for the metrics are unique. Rather, some wavenumbers are common between two or more metrics. For example, from FIG. 3A, for metric number 1, 2 circles are shown, for 2 unique wavenumbers, while for metric number N=100, about 56 circles are shown, for 56 unique wavenumbers (rather than 200 circles if all wavenumbers for the 100 best metrics were unique).

It is clear from the distinct form of the graphs in FIG. 3 that there are significant differences in the wavelengths selected for discrimination between these four cell types. For example, very different behaviour is seen in the graphs of FIG. 3C and FIG. 3D for the CAM and ATM cells respectively. These differences highlight the clear discrimination achieved between these two cell types via the method of FIG. 1A. For example, FIG. 3C shows that the higher scoring metrics for discriminating CAM from ATM, OE19 and OE21 are those that contain at least one wavenumber around 1750 cm$^{-1}$. In contrast, FIG. 3D shows a different situation is found for the ATM cell line, where higher scoring metrics are often associated with at least one comparatively low wavenumber around 1150 cm$^{-1}$. This is a significant result because Histopathologists find it difficult to distinguish between these cell types using the known methods of performing optical microscopy on Haematoxylin and Eosin stained samples.

The second mathematical function may take other forms than that discussed above. As further examples, the second mathematical function may be any of the following equations:

$$score = success\ rate \times confidence\ value$$

$$score = (success\ rate)^2 \times confidence\ value$$

$$score = success\ rate \times (confidence\ value)^2$$

$$score = (success\ rate)^2 \times (confidence\ value)^2$$

$$score = success\ rate \times (1 - mislabelling\ rate)^2$$

In one preferred embodiment, the second mathematical function is the following equation:

$$score = success\ rate \times (1 - mislabelling\ rate)^2$$

The fourth sub-step S7D in the method of FIG. 1C includes determining aggregate success rates for combinations of the metrics. The aggregate success rates may be calculated for every combination of the metrics. The aggregate success rates may be calculated for combinations of at least the higher ranking metrics, e.g. up to the top 500, up to the top 400, up to the top 300, up to the top 200, up to the top 100, or up to the top 50, 40, 30, 20, 10 or 5 ranking metrics. The aggregate success rates may be calculated by using the allocations of the first portion of spatial regions associated with two of the highest ranked metrics to determine an average allocation of the first portion of spatial regions. An aggregate success rate associated with the average allocation may then be determined by determining how often the average allocation is correct. This step may be repeated using an increasing number of the higher ranked metrics. Discrimination between the cell or tissue types using multiple higher ranked metrics advantageously reduces the sensitivity of the method to random noise and small variations in absorption spectra within a given cell or tissue type. Determining an aggregate success rate advantageously gives an overview of the preferred number of metrics to be used to give the best overall success rate for discrimination of the cell or tissue types.

The aggregate success rate may be plotted as a function of the number of metrics used to produce the aggregate success rate, which indicates a preferred number of metrics required to achieve improved discrimination between the first cell or tissue type and the different cell or tissue type. The number of higher ranked metrics that produce the highest success rate may be considered to be the preferred number of metrics to use to achieve the greatest discrimination accuracy. However, for practical purposes it may be desirable to use a number of higher ranking metrics that is less than the number required to give the highest success rate. This may for instance be the case where a lower number of metrics nonetheless provides a degree of discrimination accuracy that is adequately high for a given purpose. This will have the advantage of providing a suitable degree of accuracy in a shorter time and/or with less computational effort.

FIG. 4 shows a graph of the aggregate success rates for the four cell types discussed in relation to FIG. 2 and FIG. 3. The graphs show how, for each cell type, the aggregate success rate varies with an increasing number of higher ranked metrics used in the fourth sub-step S7D of the method of FIG. 1C. Different variation is demonstrated for the different cell types. For example, the aggregate success rate for the ATM cell line increases with the number of metrics used up to 24 metrics and subsequently decreases. In contrast, the aggregate success rate for OE19 is high for a low number of metrics and decreases as more metrics are included. For each cell type, a preferred number of higher ranked metrics to be used for discrimination may be determined by the position of the maximum aggregate success rate.

The fifth sub-step S7E in the method of FIG. 10 includes selecting wavelengths that are associated with a greater aggregate success rate. At least wavelengths associated with the greatest aggregate success rate may be selected. Selecting the wavelengths associated with a greater aggregate success rate may involve comparing each aggregate success rate to the number of metrics used to obtain the aggregate success rate. The wavelengths that are associated with the metrics for which the aggregate success rate is greater than a desired aggregate success rate may be selected as the sub-group of wavelengths. The number of metrics for which the aggregate success rate is at its highest may be referred to as the optimum number of metrics because that number of metrics provides the most accurate discrimination of the cell or tissue types.

The aggregate success rate may vary in different ways for different cell or tissue types. Referring again to FIG. 4, it can be seen that the aggregate success rate for ATM increases for each metric up until 24 metrics are used, after which, the aggregate success rate decreases. In contrast, the aggregate success rate for OE19 is relatively high for a relatively low number of metrics and decreases as more metrics are used.

Experimental Methods

Below is a discussion of the experimental set-ups used to generate the data shown in FIGS. 2-7 and tables 1-4.

Experiments were conducted on two esophageal cancer cell lines (OE19 and OE21) and two esophageal myofibroblast cell lines denoted CAM (cancer associated) and ATM (adjacent tissue associated). CAMs and ATMs were derived from esophageal adenocarcinoma and macroscopically adjacent normal tissues obtained at surgery from the same patient. Of the two tissue samples one was cancerous and the other Barrett's, respectively. The OE19 and OE21 human Caucasian esophageal cells were obtained from HPA Culture Collections (Sigma, Dorset, UK). Cells were cultured at 37° C. in a 5% $CO_2$ atmosphere in Roswell Park Memorial Institute (RPMI 1640) growth media (Sigma) supplemented with 2 mM glutamine (Sigma), 10% v/v foetal bovine serum (FBS) (Invitrogen, Paisley, UK) and 1% v/v penicillin/streptomycin (Sigma) until they reached 70-80% confluence. The culture medium was replenished at two-day intervals. The myofibroblast cells were cultured at 37° C. in a 5% $CO_2$ atmosphere in Dulbecco's modified Eagle medium with L-glutamine containing 10% v/v FBS, 1% v/v modified Eagle medium nonessential amino acid solution, 1% v/v penicillin/streptomycin, and 2% antibiotic-antimycotic. Medium was replaced routinely every 48-60 hours and cells were passaged at confluence, up to 12 times. $CaF_2$ discs (20 mm diameter×2 mm thick, Crystran Ltd, Poole, UK) were sterilized using ethanol and rinsed with ultra-pure water and left to air-dry overnight. The discs were irradiated with UV for 30 minutes to ensure sterility. The sterile discs were then placed in each well of a tissue culture twelve-well plate (Corning, New York, USA). The cells ($2\times10^4$ $mL^{-1}$) were seeded on each disc and incubated in a 5% $CO_2$ incubator at 37° C. for two-days. After two-days the media was removed and the cells were fixed with a 4% v/v paraformaldehyde (PFA) (Sigma) solution and stored in 1× phosphate buffered saline (PBS) solution at 4° C. until required. Prior to imaging the $CaF_2$ slide containing the fixed cells was rinsed at least three times with Millipore ultra-pure water (18 MD cm). The rinsed slide was then removed from the well plate, the back surface wiped with ultra-pure water to ensure complete removal of any phosphate residue and then left to dry in the slide holder for a minimum of 90 minutes.

Following appropriate ethical committee approval and informed patient consent, esophageal biopsy samples were obtained using standard biopsy forceps from patients attending for diagnostic esophago-gastro-duodenoscopy at Royal Liverpool and Broadgreen University Hospitals NHS Trust. Biopsies were obtained from patients with Barrett's esophagus (with no histological evidence of dysplasia) and from patients with Barrett's associated esophageal adenocarcinoma. These were fixed in 10% formalin and embedded in paraffin wax. Histological diagnosis was confirmed following H&E staining by a Consultant Gastrointestinal Histopathologist as part of routine patient care. Serial 5 µm sections from each paraffin block were subsequently cut using a microtome, mounted on calcium fluoride discs, and dewaxed using xylene.

FTIR studies of the cell lines and tissue sections were carried out in transmission with a Varian Cary 670-FTIR spectrometer in conjunction with a Varian Cary 620-FTIR imaging microscope produced by Varian (now Agilent Technologies, Santa Clara Calif., USA) with a 128×128 pixel mercury-cadmium-telluride (MCT) focal plane array. FTIR images were acquired with a spectral range from 990 $cm^{-1}$ to 3800 $cm^{-1}$ with a resolution of 2 $cm^{-1}$, co-adding 256 scans. Infrared spectra were initially pre-processed using a principal component analysis based noise reduction algorithm. Substantial improvements in signal-to-noise were observed by retaining 10 principal components without the loss of biologically significant information. Spectra were then quality checked to remove those not attributable to the cell (including blank regions of the sample), or to a high degree of scattering. The quality check utilized a threshold based on the height of the Amide I band with spectra having absorbance between 0.03 and 1.00 being retained. Finally infrared spectra were corrected for resonant Mie scattering with the RMieS-ESMC algorithm using 80 iterations and a matrigel reference spectrum.

Experimental Data and Discussion

An FTIR data cube was acquired for each cell type and were corrected for Mie scattering effects. Each FTIR data cube consists of an image of i×j pixels (typically i×j=5000), where the third dimension is the FTIR spectra of 1406 data points covering the range of wavenumbers v=990 $cm^{-1}$ to 3800 $cm^{-1}$ in 2 $cm^{-1}$ steps. The FTIR image obtained from the OE19 sample is shown in FIG. 8A. The FTIR spectra characterizing each cell type (FIG. 8B) over the "fingerprint region" of 1000 $cm^{-1}$ to 1800 $cm^{-1}$, were generated from averaging the spectra obtained from each pixel in the corresponding FTIR image of that cell type. This average does not include pixels from blank areas of the image. There are problems in deducing information from a direct comparison of these average profiles. Firstly due to variations in the total intensity of the spectra obtained from each specimen, it is necessary to normalize each profile to the same area under the curve. Since the effect of the normalization on the spectral profile depends on the wavelength range used this can hide or exacerbate differences between the profiles of different specimens. Finally the standard deviation of the absorbance of all pixels at a given wavenumber is significant and shows significant overlap between cell types (FIG. 10). Consequently a more sophisticated analysis is required to reveal the differences between the spectral profiles of the different cell lines. This is obtained using a multivariate analysis method hereafter referred to as Metrics Analysis (MA). The metrics were chosen to be the ratios of the absorbance for a given pair of wavenumbers. Importantly, this MA method treats all the data equally and does not attribute any biological significance to any particular wavenumber, in contrast to conventional approaches in which discrimination of tissues uses metrics that are defined to have a significance related to tissue biochemistry. By examining ratios at wavenumbers over the whole range of 1000 $cm^{-1}$ to 1800 $cm^{-1}$, the MA demonstrates the existence of biomarkers at wavenumbers that have not been identified in previous studies using other analysis techniques.

The MA method can be divided into three main parts: Stage 1: Training, Stage 2: Testing, and Stage 3: Analysis. For the results reported here, training was completed using 75% of the number of spectra in the data set, which were chosen at random, and testing was undertaken on the remaining 25%. Stage 1 parameterizes each cell type via the calculation of the absorbance ratio at two wavenumbers–the metric. This was done for all wavenumber combinations at a chosen step size over the range 1000 $cm^{-1}$ to 1800 $cm^{-1}$. The step size was 6 $cm^{-1}$, as anything smaller has been shown to be unnecessary. As a consequence there are a total of ~18000 metrics. In Stage 2 a score was then associated with each metric to quantify how well the metric was able to discriminate between cell types. For each cell type, scores were calculated by making distribution histograms for the metrics (one for the cell type and one for each of the other cell types in the analysis) where a high score is obtained for distributions that are distinct and hence have relatively little overlap. The score is defined by $$\text{score} = \text{success rate} \times (1-\text{mislabelling rate})^2$$

where the success rate (often referred to as the sensitivity) is the rate at which the cell type is labeled correctly and the mislabeling rate (often referred to as the false positive rate) is the rate at which other cell types are labeled incorrectly as this cell type. Given that for the 25% of spectra used in this testing phase, the cell type is known, a success rate can be calculated and the probabilities of identifying the other cell types are used to determine the mislabeling rate. The scores for each metric are used to rank the ability of that metric to distinguish a given cell type. Stage 3 determines the number of metrics that are needed by a voting system to give the best overall success rate for cell type discrimination. The overall success rate is plotted as a function of the number of metrics used which indicates the optimal number of metrics required to achieve the best discrimination.

The wavenumbers that the MA method finds to be most important for discrimination can be visualized in a plot of the metric scores against $v_1$ and $v_2$, hereafter referred to as a Butterfly Plot. Four such plots, for CAM and ATM, are shown in FIG. 2, as detailed previously. Generally, the Butterfly Plots may be considered as heat maps in which heat is represented by the metric score such that red corresponds to a relatively higher metric score and blue corresponds to a relatively lower metric score. The Butterfly Plots are symmetric about the line $v_1=v_2$. All possible metrics are shown in these plots. The color-bar scale ranges from the least important (blue) to most important (red) metrics for discrimination. For the CAM and ATM samples, very different behavior is seen in the Butterfly plots, which highlights the clear discrimination achieved between these two cell types. This is a significant result since histopathologists find it difficult to distinguish between these cell types using the current 240 standard method of optical microscopy on H&E stained samples. For CAM, high scoring metrics are those that contain at least one high wavenumber around 1750 cm$^{-1}$ (the red regions in FIG. 2C). The opposite situation is found for ATM, where high scoring metrics are often associated with at least one low wavenumber around 1150 cm$^{-1}$ (the red regions in FIG. 2D).

While the scores for all the possible metrics (at the chosen step size) are evaluated and shown in FIG. 2, further insight can be obtained by limiting the results to a visualization of the best (highest-scoring) 100 metrics, hereafter referred to as Manhattan Plots. The plots for CAM and ATM are shown in FIG. 3, where the highest-ranked metrics for each cell type are shown plotted for $v_1$ (red) and $v_2$ (blue). These plots illustrate the combinations of wavenumbers that are used as a function of an increasing number of metrics from 1 to 100. It is clear that there are significant differences in the wavenumbers used for discrimination between these two cell types.

In addition to visualizing the metric scores by Butterfly and Manhattan Plots, the success rate can be presented in a plot (FIG. 4) that shows how, for each cell type, the success rate varies with increasing number of metrics used in the analysis. In general, the success rate will eventually diminish due to poor metrics being added that compromise the success rate. Different variation is seen for the different cell types. For example, the success rate for ATM increases with the number of metrics used up to 24 metrics and subsequently decreases. In contrast, the success rate for OE19 is high for a low number of metrics and decreases as more metrics are used. For each cell type, the optimum number of metrics required for discrimination is given by the position of the maximum success rate. As the data were sampled from a single image for each cell line, there was concern over whether spectra from adjacent pixels, which may be correlated due to the finite spatial resolution of the imaging system, could potentially bias the analysis and hence result in unrealistically high scores. To check this, the spatially ordered spectra were split into training and testing sets in such a way that the vast majority of the training spectra were not adjacent to the testing spectra. This analysis returned results that were indistinguishable from the original sets, demonstrating that any such pixel correlations do not contribute any significant bias to the results.

Table 1 below shows the wavenumbers from the top five metrics for each of the four cell types discussed in relation to FIG. 2, FIG. 3 and FIG. 4.

TABLE 1

Summary of Cell Line Metrics

| Cell Type | Optimum Number of Metrics | Success Rate (%) | Wavenumbers for the top five metrics (cm$^{-1}$) |
| --- | --- | --- | --- |
| OE19 | 2 | 97 | 1375, 1381, 1400, 1406, 1418, 1692, 1697 |
| OE21 | 1 | 81 | 1443, 1449, 1466, 1472, 1539, 1545, 1551 |
| CAM | 64 | 92 | 1443, 1508, 1522, 1678, 1684, 1692 |
| ATM | 24 | 91 | 1049, 1103, 1146, 1200, 1206, 1400, 1424, 1466, 1472 |

The optimum number of metrics varies between each cell type. The same wavenumber may appear in a plurality of the top five scoring metrics for a given cell type, thus the number of wavenumbers for the top five scoring metrics may vary between different cell types. When used to discriminate between the cell types above, the method according to the first aspect is able to achieve accuracies of between 81% and 97%. The wavenumbers that are found to discriminate between the different cell types differ significantly from the wavenumbers that have previously been used to characterize esophageal tissue types. A wavenumber that is common to two or more cell types means that the wavenumber discriminates between those cells types and all the others. It is understood that this means that the wavenumber (or wavelength) is likely to be characteristic of a chemical moiety that is either present or absent in those cells types in a concentration that is significantly different to its concentration in all other cell types.

To aid the interpretation of the wavenumbers that are found to be important in this analysis, the wavenumbers in the top five metrics are examined for each cell type. Five metrics were chosen to give an apposite number of wavenumbers to allow meaningful comparisons between values for different cell types. These wavenumbers are shown in FIG. 5 and summarized in Table 1, and will be discussed further in the Discussion section.

FIG. 5 shows four graphs of the importance of the wavenumbers associated with the five highest scoring metrics for the OE19, OE21, CAM and ATM cell lines. As can be seen from the graphs of FIG. 5, each cell type has a distinct set of important wavelengths, each of which are found by the method of FIG. 1A. The importance of a wavenumber may correspond to the frequency with which the wavenumber is found to be useful in the discriminating process. That is, importance of a wavenumber may correspond to the number of times that wavenumber occurs in the higher scoring metrics.

The following is a discussion of the application of the method of FIG. 1A to four different tissue samples. Endoscopic biopsies were obtained from a patient with Barrett's esophagus (with no histological evidence of dysplasia) and from a patient with Barrett's associated esophageal adenocarcinoma. From these samples, four different tissue types were identified via histological diagnosis by a Consultant Gastrointestinal Histopathologist: cancerous tissue, cancer associated stroma, Barrett's tissue and Barrett's associated stroma. The method of FIG. 1A achieved discrimination of these tissue types with an average success rate of 85%. The results for the tissue types are shown in FIG. 6 and FIG. 7.

FIG. 6 shows a graph of the aggregate success rates for four different tissue types, cancerous tissue, cancer associated stroma (CAS), Barrett's tissue and Barrett's associated stroma (BAS). As was the case with the cell types shown in FIG. 4, the aggregate success rate for the tissue types varies with an increasing number of higher ranked metrics used in the fourth sub-step S7D of the method of FIG. 1C. Different variation is demonstrated for the different tissue types. As was the case for the cell types of FIG. 4, for each tissue type of FIG. 6 a preferred number of higher ranked metrics to be used for discrimination may be determined by the position of the maximum aggregate success rate.

FIG. 7 shows four graphs of the importance of the wavenumbers associated with the five highest scoring metrics for the Cancerous tissue, CAS, Barrett's tissue and BAS samples of FIG. 6. The graphs show the wavenumbers that discriminate between the four tissue types for the top five metrics. As can be seen from the graphs of FIG. 7, each tissue type has a distinct set of important wavelengths, each of which are found by the method of FIG. 1A.

Table 2 below shows the wavenumbers from the top five metrics for each of the four tissue types discussed in relation to FIG. 6 and FIG. 7.

TABLE 2

Summary of Cell Line Metrics

| Tissue Type | Optimum Number of Metrics | Success Rate (%) | Wavenumbers for the top five metrics (cm$^{-1}$) |
|---|---|---|---|
| Cancerous tissue | 83 | 88 | 1460, 1466, 1472, 1480, 1485 |
| Cancer associated stroma | 295 | 71 | 999, 1007, 1018, 1061, 1067, 1073 |
| Barrett's tissue | 33 | 93 | 1375, 1406, 1412, 1418, 1443, 1449, 1466 |
| Barrett's associated stroma | 125 | 87 | 1146, 1152, 1225, 1231, 1236, 1661 |

As was the case for the cell types shown in table 1, the optimum number of metrics varies between each tissue type in table 2. The method of FIG. 1A achieves accuracies of between 71% and 93% for the four different tissue types. The wavenumbers that are found to discriminate between the different tissue types differ significantly from the wavenumbers that have previously been used to characterize esophageal tissue types. As was the case with table 1, for table 2 a given wavenumber that is common to two or more tissue types means that the wavenumber discriminates between those tissue types and all the others. This means that the given wavenumber (or wavelength) is a characteristic of a chemical moiety that is either present or absent in those tissue types in a concentration that is significantly different to its concentration in all other tissue types. On comparison between table 1 and table 2 it can be seen that, in general, the tissue samples generally require more metrics to be used in the analysis for more accurate discrimination than the cell line samples. This is expected given the more heterogeneous nature of chemical moieties present when considering tissue samples compared to cell samples.

The following is a discussion of the method of FIG. 1A compared to a known "random forest" method of selecting discriminating wavelengths. In order to compare the method of FIG. 1A with the known random forest method that has used previously for FTIR data analysis, the same datasets were analysed using both techniques for (i) the four cell lines discussed above in relation to FIGS. 2-5 and (ii) the four esophageal tissue types discussed above in relation to FIGS. 6 and 7. The random forest method used was used to construct a classifier to discriminate between the different samples. Table 3 below compares the results of the random forest method with the results of the method according to an embodiment for the four different cell lines OE19, OE21, CAM and ATM.

In order to compare the MA method with existing classification methods we chose a quantitative comparison with the well-established random forest (RF) method. This is the most appropriate comparison as RF encapsulates both feature extraction and classification, and is commonly used for FTIR data analysis in the biomedical field. The same datasets were analyzed using both techniques for the four cell lines. The RF method used was a standard RF classification algorithm available from https://github.com/tingliu/random-forest-matlab that was used to construct a classifier to discriminate between the different samples. Table 3 compares the MA and RF analysis results for the cell lines. The key wavenumbers found to be necessary for discrimination in both techniques showed some similarities. Little improvement in accuracy was seen when running the RF analysis for greater than ~30 seconds or by increasing the number of trees from 10 to 500. In general the MA method achieves greater accuracy in discrimination (particularly for ATM) in a shorter time (Table 3) than RF. For example, the MA of OE21 achieves a success rate of 79% within one minute whereas RF is limited 18 to ~50%. It appears that RF is unable to distinguish ATM, with success rates no higher than would be expected from random chance (25%) when choosing one cell type from four possible types. These low success rates for the RF method are a consequence of the size of the data sets (the number of spectra) associated with each of the cell lines. The MA method gives high success rates regardless of whether the data sets are balanced and of comparable sizes, whereas the RF method is sensitive to this balance and gives poor success rates unless the data sets are rebalanced or the input data are reweighted.

TABLE 3

Success rates (%) obtained by the metric analysis (MA) and random forest (RF) approaches, for the OE21 cell lines.

| | Random Forest | | Metric Analysis | |
|---|---|---|---|---|
| Number of trees | 10 | 500 | N/A | N/A |
| Resolution (cm$^{-1}$) | 20 | 20 | 20 | 6 |
| Computation time (s) | 27 | 1278 | 12 | 87 |
| OE19 success rate (%) | 94 | 96 | 85 | 97 |
| OE21 success rate (%) | 51 | 54 | 79 | 81 |
| CAM success rate (%) | 94 | 96 | 83 | 92 |
| ATM success rate (%) | 18 | 10 | 79 | 90 |
| Mean of the four cell types (%) | 64 | 64 | 81 | 90 |

The key wavenumbers found to be necessary for discrimination in both techniques showed some similarities. Little improvement in accuracy was seen when running the random forest analysis for greater than about 30 seconds or by increasing the number of trees from 10 to 500. In general, the method according to an embodiment achieves greater accuracy in discrimination (particularly for ATM) in a shorter time (compared to the random forest method. For example, the method according to an embodiment for OE21 achieves a success rate of 79% within one minute whereas the random forest method is limited to a success rate of about 50%. It appears that the random forest method is unable to distinguish ATM, with success rates no higher than would be expected from random chance (25%) when choosing one cell type from the four possible types.

Table 4 below compares the results of the random forest method with the results of the method according to an embodiment for the four different tissue types cancerous tissue, cancer associated stroma (CAS), Barrett's tissue and Barrett's associated stroma (BAS).

TABLE 4

Success rates (%) obtained by the metric analysis (MA) and random forest (RF) approaches, for the tissues types.

|  | Random Forest | | Metric Analysis | |
| --- | --- | --- | --- | --- |
| Number of Trees | 500 | 5000 | N/A | N/A |
| Resolution (cm$^{-1}$) | 20 | 20 | 10 | 4 |
| Time (s) | 63 | 648 | 31 | 246 |
| Cancerous tissue success rate (%) | 89 | 88 | 87 | 88 |
| Cancer associated stroma success rate (%) | 50 | 54 | 69 | 71 |
| Barrett's tissue success rate (%) | 83 | 82 | 93 | 93 |
| Barrett's associated stroma success rate (%) | 89 | 88 | 88 | 87 |
| Mean of the four tissue types' success rate (%) | 78 | 78 | 84 | 85 |

For the four tissue types analysed, the comparisons between the results of the method according to an embodiment and the known random forest method reveal closer agreement compared to those for the cell lines. As can be seen by Table 4, the ability of the two methods to discriminate cancerous tissue is similar. The method according to an embodiment achieves success rates that are about 10% higher for the identification of Barrett's tissue. The method according to an embodiment achieves success rates that are about 20% higher for the identification of cancer associated stroma tissues. Overall, a higher mean success rate was obtained for tissue discrimination, in a significantly shorter time, for the method according to an embodiment when compared to the known random forest method.

The wavelengths of radiation that are found to discriminate between the different cell and tissue types discussed in relation to Tables 1 and 2 via the method of FIG. 1A differ significantly from the wavelengths that have previously been used to characterize esophageal tissue types.

The meaning of the wavelengths found to discriminate between cell and tissue types in the method of FIG. 1A is subtle since the wavelengths are derived from a blind pair wise comparison of all the wavelengths in the FTIR spectra of all the cell types and separately all the tissue types. Consequently the discriminating wavelengths must be interpreted with care. When used in combination with other metrics, the selected wavelengths provide excellent discrimination between all the cells and tissue types.

Discussion

There have been significant advances in the application of FTIR to the study of normal and cancerous esophageal tissues. For example, FTIR profiles of normal and cancerous tissue have been compared and revealed prominent absorption changes at certain wavenumbers. For example, changes at 964 cm$^{-1}$ and 1237 cm$^{-1}$ have been assigned to increased nucleic acid content in malignant tissue, indicating that glycogen was clearly present in healthy tissue but almost completely depleted in cancerous tissue. For example, using a partial least squares fitting procedure, the principal components of the FTIR spectra of squamous, Barrett's non-dysplasia, Barrett's dysplasia and gastric tissue in the range 950 cm$^{-1}$ to 1800 cm$^{-1}$ may arise from variations in the concentration of DNA, protein, glycogen and glycoprotein. Dysplasia may characterized by an increase in glycoprotein and DNA. For example, an imaging study using a combination of confocal FTIR microscopy and a hierarchical cluster analysis of second derivative FTIR spectra has distinguished normal and Barrett's esophageal tissue from adenocarcinoma and confirmed the association of glycoprotein bands with Barrett's and located these at the edge of crypts. For example, a rapid IR mapping automated analysis technique identifies Barrett's dysplasia or adenocarcinoma with 95.6% sensitivity and 86.4% specificity. Such analysis of second derivative FTIR spectra confirmed that normal squamous tissue has a high glycogen content, Barrett's tissue a high glycoprotein content and Barrett's dysplasia and adenocarcinoma a high DNA content.

However, the first thing to note from the results of the MA described herein according to the first aspect is that the wavenumbers that are found to discriminate between the different cell types (Table 1) differ significantly from the wavenumbers that have previously been used to characterize esophageal tissue types. For example, none of the glycogen, glycoprotein or DNA wavenumbers identified using a conventional method appear in Table 1. Also, only four of the twenty characteristic wavenumbers identified as distinguishing normal tissue from adenocarcinoma by another conventional method appear in Table 1. This does not mean that the wavenumbers identified using conventional methods are not valid discriminants (indeed, they are found by the MA when more metrics are included) but that they are not as significant as those found from the top five metrics.

The four wavenumbers common to this work the another conventional method provide discriminants, to an accuracy of ±1 cm$^{-1}$, of the following cells from all other cells; ATM (1049 cm$^{-1}$), OE19 and ATM (1399 cm$^{-1}$), OE19 and ATM (1465 cm$^{-1}$) and OE21 (1545 cm$^{-1}$). These wavenumbers may be attributed to glycogen, lipids, lipids and proteins. The meaning of the wavenumbers found to discriminate between cell types in the MA is subtle since they are derived from a blind pair wise comparison of all the wavenumbers in the FTIR spectra of all the cell types. Consequently the discriminating wavenumbers must be interpreted with care. What is clear is that when used in combination with other metrics they provide excellent discrimination between all the cell types (FIG. 5). An analysis at the level of five metrics reveals twenty-four discriminating wavenumbers and as described in detail above, only four of these wavenumbers have been used in previous work to characterize differences between esophageal tissue types. Five of these discriminating wavenumbers in Table 1 are common to more than one cell type. A wavenumber that is common to two cell types means that it discriminates between those cells and all the others. This means that it is a characteristic of a chemical moiety that is either present or absent in those cells in a concentration that is significantly different to its concentration in all other cells. The finding from previous work that malignancy is characterized by an increase in DNA and a large decrease in glycogen suggests that changes in the concentration of these molecules should provide important discriminants between the ATM cells, which can be taken to be representative of healthy tissue, and the CAM cells and two malignant cell lines. This draws attention to the region between 1000 cm$^{-1}$ and 1200 cm$^{-1}$ where there is significant overlap between strong contributions from both molecules and Table 1 and FIG. 5 show a strong concentration of discriminating wavenumbers in this spectral region.

FIG. 9 shows an overlay of the normalized spectral profiles of FIG. 8A for each cell type in this spectral region. As explained earlier such comparisons of spectra can be misleading due to the dependence of the profiles on the wavelength range over which the normalization is carried out. However by taking a third power derivative of the spectra obtained from normal and malignant tissue, four key wavenumbers have been identified previously using conventional methods in this region: 1024 cm$^{-1}$, 1049 cm$^{-1}$, 1080 cm$^{-1}$ and 1155 cm$^{-1}$ which may be attributed to glycogen, glycogen, nucleic acids and proteins respectively. Only one of these wavenumbers, 1049 cm$^{-1}$, occurs in the list of discriminating wavenumbers of Table 1 and FIG. 5. A deeper analysis of the data at the optimum number of metrics, twenty-four, reveals a large increase in the number of discriminating wavenumbers in this range as shown in FIG. 9. None of these additional wavenumbers correspond to the wavenumbers identified previously using conventional methods. It is possible that some of the discriminating wavenumbers shown in FIG. 9 arise from particular chemical or structural 406 effects in the DNA of the OE19, OE21 and CAM cell lines which could not be identified from tables of wavenumbers known to arise from particular chemical moieties.

A comparison of the other wavenumbers that discriminate between the different cell types and with the signatures of known chemical moieties provides other insights into differences in chemical structure of the cells and tissues. For example the OE19 and CAM cells, which are both derived from adenocarcinoma, share a discriminant at 1692 cm$^{-1}$ associated with nucleic acids, which is absent from OE21 cells, which arise from squamous carcinoma. This wavenumber may be a moiety that is specific to adenocarcinoma. The OE21 and ATM cells share discriminating wavenumbers of 1466 cm$^{-1}$ and 1472 cm$^{-1}$, which have been identified as characteristics of lipids. It is particularly notable that the metrics approach provides excellent discrimination between cells derived from adenocarcinoma (OE19) and squamous cell carcinoma (OE21) and that ATM and CAM cells do not share a single one of the fifteen wavenumbers that discriminate between them and the other cell types. Clearly the identification of discriminating wavenumbers between the various cells types contain a wealth of information that is worthy of further study and may produce significant new insights into the chemical structure of esophageal and other cancers.

Summary

A method of selecting wavelengths of radiation for discriminating a first cell or tissue type from a different cell or tissue type is described. First and second sets of absorption spectra are obtained, each set comprising spectra obtained at a plurality of different spatial regions of the first cell or tissue type and of the different cell or tissue type, respectively. Sets of corresponding metrics are defined for the first and second sets of absorption spectra for each spatial region. Each metric comprises information corresponding to the absorption for at least two different wavelengths. The metrics in each set comprise different combinations of wavelengths. A characteristic value is generated for each metric. Distributions are generated for each metric using corresponding characteristic values for the first cell or tissue type and for the different cell or tissue type and compared to determine an extent of similarity. The metrics are ranked based on the extent of similarity and wavelengths associated with higher ranked metrics, having higher similarities, are selected.

Briefly, the method according to an embodiment can discriminate, with accuracies in the range 81% to 97%, between FTIR images of esophageal cancer OE19, OE21, CAM and ATM cell lines. This provides the first accurate discrimination between CAM and ATM myofibroblast cells taken within 3 cm of tissue from the same patient. This is a significant result since Histopathologists find it difficult to distinguish between these cell types using the current standard method of optical microscopy on H&E stained samples. The method according to an embodiment offers a new way of interpreting FTIR data. The method has revealed wavelengths of radiation which uniquely discriminate between all four different cell and tissue types, many of which have not previously been identified with chemical moieties found in healthy tissue. The method according to an embodiment discriminates between different cell and tissue types with high accuracy and speed and has significant advantages over the known random forest method. The method according to an embodiment is expected to be widely applicable to other cell types and tissues due to the large variety of chemical bonds found in biological samples.

In more detail, the inventors have demonstrated that a novel multivariate statistical analysis technique can discriminate with accuracies in the range 81% to 97% between FTIR images of OE19, OE21, CAM and ATM cell lines. This provides the first accurate spectral discrimination between CAM and ATM myofibroblast cells taken within 3 cm of tissue from the same patient. It should be stressed that these cell types are not readily distinguished by routine morphological approaches even though it is established that they have important biochemical differences that are relevant to the stimulation of cancer cell behavior. The findings have potential clinical application in early diagnosis by identification of putative cancer cell microenvironments and by allowing the demarcation between tumor and adjacent tissue stroma without recourse to the analysis of biomarkers or extensive tissue processing. This is a significant result since histopathologists find it difficult to distinguish between these cell types using the current standard method of optical microscopy on H&E stained samples. Moreover, the data indicate that it is now justified to conduct a much larger, appropriately powered, trial directed at the spectral discrimination of the important clinical groups, not least those Barrett's patients most at risk of progression including those with dysplastic lesions. The MA method offers a new way of interpreting FTIR data. It has revealed wavenumbers which uniquely discriminate between all four cell types, many of which have not previously been identified with chemical moieties found in healthy tissue. The method discriminates between cells types with high accuracy and speed and has significant advantages over the RF approach. The method is expected to be widely applicable to other cell types and tissues.

Where the context allows, embodiments may be implemented in hardware, firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic storage media; optical storage media; flash memory devices; electrical, optical, acoustical or other forms of propagated signals (e.g. carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc. and in doing that may cause actuators or other devices to interact with the physical world.

While specific embodiments have been described above, it will be appreciated that the invention may be practised otherwise than as described. The descriptions above are intended to be illustrative, not limiting. Thus it will be apparent to one skilled in the art that modifications may be made to the invention as described without departing from the scope of the claims set out below.

The invention claimed is:

1. A method of selecting wavelengths of radiation capable of discriminating a first cell or tissue type from a different cell or tissue type for use in radiation absorption spectroscopy, the method comprising:
    obtaining a first set of absorption spectra comprising an absorption spectrum obtained at each spatial region of a plurality of different spatial regions of the first cell or tissue type and obtaining a second set of absorption spectra comprising an absorption spectrum obtained at each spatial region of a plurality of different spatial regions of the different cell or tissue type;
    defining a set of metrics for each spatial region belonging to the first set of absorption spectra and defining a corresponding set of metrics for each spatial region belonging to the second set of absorption spectra, wherein each metric comprises information corresponding to the quantities of radiation absorbed for at least two different wavelengths for the given spatial region and wherein the metrics in a set comprise different combinations of wavelengths;
    performing a first mathematical function on each metric to generate a characteristic value for each metric, wherein the characteristic value is dependent on the amount of radiation absorbed at each of the at least two different wavelengths belonging to the metric;
    generating a distribution comprising the characteristic values of a given metric across the plurality of spatial regions belonging to the first cell or tissue type, and generating a corresponding distribution comprising the characteristic values of the same given metric across the plurality of spatial regions belonging to the different cell or tissue type and repeating for each of the metrics;
    for each metric, comparing the distributions generated for the first cell or tissue type and the different cell or tissue type for a given metric, and determining an extent of similarity between the distributions;
    ranking the metrics based on the extent of similarity between the distributions belonging to the metrics, wherein metrics associated with distributions having less similarity rank higher than metrics associated with distributions having more similarity; and
    selecting the wavelengths of radiation associated with the higher ranked metrics.

2. The method of claim 1, wherein the distributions are treated as probability distribution functions and the metrics are ranked by quantifying the extent of similarity between the probability distribution functions, and wherein the extent of similarity between the probability distribution functions is quantified by using parameters of the probability distribution functions.

3. The method of claim 1, wherein the first cell or tissue type is known and wherein a first portion of spatial regions are not used to generate the distributions, and wherein the method further comprises defining a success rate for each higher ranked metric, the success rate being determined by:
    using the higher ranked metrics to allocate each spatial region in the first portion of spatial regions to either the first cell or tissue type or the different cell or tissue type;
    determining the number of spatial regions of the first portion of spatial regions that were correctly allocated using the higher ranked metrics; and
    calculating the success rate of a higher ranked metric as being how often the higher ranked metric correctly assigned spatial regions of the first portion of spatial regions to either the first cell or tissue type or the different cell or tissue type.

4. The method of claim 3, wherein the characteristic values for the first portion of spatial regions are compared with the probability density functions in order to allocate each of the spatial regions of the first portion to either the first cell or tissue type or the different cell or tissue type.

5. The method of claim 3, wherein the method further comprises defining a mislabeling rate for each higher ranked metric, the mislabeling rate being the probability that the higher ranked metric identified the different cell or tissue type as being the first cell or tissue type.

6. The method of claim 3, further comprising scoring the higher ranked metrics by performing a second mathematical function on the calculated success rates and mislabeling rates and comparing outcomes of the second mathematical function, preferably wherein the second mathematical function is:

$$\text{score} = \text{success rate} \times (1 - \text{mislabelling rate})^2$$

7. The method of claim 6, further comprising determining aggregate success rates for a plurality of combinations of the higher ranked metrics, the aggregate success rates being calculated by:
    using the allocations of the first portion of spatial regions associated with two of the highest ranked metrics to determine an average allocation of the first portion of spatial regions and determining an aggregate success rate associated with the average allocation by determining how often the average allocation is correct; and
    repeating this step using an increasing number of the higher ranked metrics.

8. The method of claim 7, further comprising:
    comparing each aggregate success rate to the number of metrics used to obtain the aggregate success rate; and
    selecting a sub-group of wavelengths that are associated with the metrics for which the aggregate success rate is greater than a desired aggregate success rate.

9. The method of claim 1, wherein the first mathematical function determines a ratio between the amounts of radiation absorbed at the at least two different wavelengths of radiation of a metric.

10. The method of claim 1, wherein the wavelengths are selected from about 500 of the highest ranking metrics.

11. The method of claim 3, wherein the portion of spatial regions used to generate the first and second distributions is greater than the portion of spatial regions used to calculate the success rates, preferably wherein about 75% of the spatial regions from the image of the first cell or tissue type are used to generate the first and second distributions and the remaining spatial regions from the image of the first cell or tissue type are used to determine the success rates.

12. The method of claim 1:
  wherein the first and second sets of absorption spectra comprise data obtained at wavelengths from about 900 cm$^{-1}$ to about 4000 cm$^{-1}$, preferably from about 1000 cm$^{-1}$ to about 1800 cm$^{-1}$; or
  wherein the first and second sets of absorption spectra are obtained using Fourier transform infrared spectroscopy, or wherein the first and second sets of absorption spectra are corrected for Mie scattering effects.

13. The method of claim 1, wherein at least one of the first cell or tissue type and/or the different cell or tissue type is cancerous.

14. A method of discriminating between multiple different cell or tissue types comprising:
  performing absorption spectroscopy on the multiple different cell or tissue types using wavelengths of radiation selected according to the method of claim 1;
  determining respective characteristic values for each of the multiple cell or tissue types according to the steps described in claim 1;
  comparing the respective characteristic values obtained by the absorption spectroscopy with distributions corresponding to known cell or tissue types for each of the multiple cell or tissue types obtained by the method of claim 1; and,
  discriminating between the multiple different cell or tissue types by determining whether or not the characteristic values obtained by the absorption spectroscopy performed on the multiple different cell or tissue types correspond to the known distributions for the known cell or tissue types for each of the multiple cell or tissue types.

15. A method of discriminating between multiple different cell or tissue types comprising:
  obtaining information corresponding to the quantity of radiation absorbed at each of a plurality of wavelengths of radiation selected according to the method of claim 1 for the multiple different cell or tissue types;
  determining respective characteristic values for each of the multiple cell or tissue types according to the steps described in claim 1;
  comparing the respective characteristic values obtained at each of the plurality of wavelengths with distributions corresponding to known cell or tissue types obtained by the method of claim 1 that are associated with the selected wavelengths for each of the multiple cell or tissue types; and
  discriminating between the multiple different cell or tissue types by determining whether or not the respective characteristic values correspond with the known distributions for the known cell or tissue types for each of the multiple cell or tissue types.

16. A method of identifying the presence or absence of a first cell or tissue type in a cell or tissue sample obtained from a patient comprising multiple different cell or tissue types, the method comprising:
  obtaining information corresponding to the quantity of radiation absorbed at each of a plurality of wavelengths of radiation selected according to the method of claim 1 and determining respective characteristic values for one or more of the cell or tissue types in the tissue sample according to the steps described in claim 1;
  comparing the respective characteristic values obtained at each of the plurality of the selected wavelengths with corresponding known distributions for the first cell or tissue type associated with the selected wavelengths for each of the cell or tissue types in the tissue sample;
  determining whether or not the respective characteristic values correspond with the known distributions for the first cell or tissue type for each of the cell or tissue types in the tissue sample; and
  when the respective characteristic values for the cell or tissue types in the tissue sample are determined to correspond with the known distributions for the first cell or tissue type, identifying the presence of the first cell or tissue type, or when the characteristic values for the cell or tissue types in the tissue sample do not correspond with the known distributions for the first cell or tissue type, determining there to be an absence of the first cell or tissue type.

17. The method of claim 16:
  wherein the first cell type is esophageal cancer cell line OE19 and the tissue sample obtained from the patient comprises one or more of esophageal cancer cell line OE21, cancer associated myofibroblast cells and adjacent tissue myofibroblast cells, and wherein the selected plurality of wavelengths of radiation correspond to at least two of the following wavenumbers (cm$^{-1}$) of radiation: 1375, 1381, 1400, 1406, 1418, 1692, 1697; or
  wherein the first cell type is esophageal cancer cell line OE21 and the tissue sample obtained from the patient comprises one or more of esophageal cancer cell line OE19, cancer associated myofibroblast cells and adjacent tissue myofibroblast cells, and wherein the selected plurality of wavelengths of radiation correspond to at least two of the following wavenumbers (cm$^{-1}$) of radiation: 1443, 1449, 1466, 1472, 1539, 1545, 1551; or
  wherein the first cell type is cancer associated myofibroblast cells and the tissue sample obtained from the patient comprises one or more of esophageal cancer cell line OE19, esophageal cancer cell line OE21, and adjacent tissue myofibroblast cells, and wherein the selected plurality of wavelengths of radiation correspond to at least two of the following wavenumbers (cm$^{-1}$) of radiation: 1443, 1508, 1522, 1678, 1684, 1692; or
  wherein the first cell type is adjacent tissue myofibroblast cells and the tissue sample obtained from the patient comprises one or more of esophageal cancer cell line OE19, esophageal cancer cell line OE21, and cancer associated myofibroblast cells, and wherein the selected plurality of wavelengths of radiation correspond to at least two of the following wavenumbers (cm$^{-1}$) of radiation: 1049, 1103, 1146, 1200, 1206, 1400, 1424, 1466, 1472; or
  wherein the first tissue type is esophageal cancerous tissue and the tissue sample obtained from the patient comprises one or more of cancer associated stroma, Barrett's tissue and Barrett's associated stroma, and wherein the selected plurality of wavelengths of radiation correspond to at least two of the following wavenumbers (cm$^{-1}$) of radiation: 1460, 1466, 1472, 1480, 1485; or
  wherein the first tissue type is cancer associated stroma and the tissue sample obtained from the patient comprises one or more of esophageal cancerous tissue, Barrett's tissue and Barrett's associated stroma, and wherein the selected plurality of wavelengths of radiation correspond to at least two of the following wavenumbers (cm$^{-1}$) of radiation: 999, 1007, 1018, 1061, 1067, 1073; or wherein the first tissue type is Barrett's tissue and the tissue sample obtained from the patient comprises one or more of esophageal cancerous tissue, cancer associated stroma and Barrett's associated stroma, and wherein the selected plurality of wavelengths of radiation correspond to at least two of the following wavenumbers (cm$^{-1}$) of radiation: 1375, 1406, 1412, 1418, 1443, 1449, 1466; or wherein the first tissue type is Barrett's associated stroma and the tissue sample obtained from the patient comprises one or more of esophageal cancerous tissue, cancer associated stroma, and Barrett's tissue, and wherein the selected plurality of wavelengths of radiation correspond to at least two of the following wavenumbers (cm$^{-1}$) of radiation: 1375, 1406, 1412, 1418, 1443, 1449, 1466.

18. The method of claim 16, further comprising, when at least one of the first cell or tissue type and the different cell or tissue type is identified being a cell or tissue type in a diseased state, contacting the diseased cell or tissue type in vitro with an active agent known to have efficacy in treating the disease, or an agent that is determined to be a therapeutic candidate for treating the disease.

19. A method of treatment of a disease in a patient wherein the method comprises identifying the presence or absence of a first cell or tissue type in a cell or tissue sample obtained from a patient according to the method as defined in claim 16 and, when the first cell or tissue type is identified as being in a diseased state or pre-diseased state, treating the respective disease.

20. A non-transitory computer-readable medium comprising a computer program stored thereon, the computer program comprising computer readable instructions that, when executed by processing circuitry of a computing device, causes the computing device to:

obtain a first set of absorption spectra comprising an absorption spectrum obtained at each spatial region of a plurality of different spatial regions of the first cell or tissue type and obtain a second set of absorption spectra comprising an absorption spectrum obtained at each spatial region of a plurality of different spatial regions of the different cell or tissue type;

define a set of metrics for each spatial region belonging to the first set of absorption spectra and define a corresponding set of metrics for each spatial region belonging to the second set of absorption spectra, wherein each metric comprises information corresponding to the quantities of radiation absorbed for at least two different wavelengths for the given spatial region and wherein the metrics in a set comprise different combinations of wavelengths;

perform a first mathematical function on each metric to generate a characteristic value for each metric, wherein the characteristic value is dependent on the amount of radiation absorbed at each of the at least two different wavelengths belonging to the metric;

generate a distribution comprising the characteristic values of a given metric across the plurality of spatial regions belonging to the first cell or tissue type, and generate a corresponding distribution comprising the characteristic values of the same given metric across the plurality of spatial regions belonging to the different cell or tissue type and repeating for each of the metrics;

for each metric, compare the distributions generated for the first cell or tissue type and the different cell or tissue type for a given metric, and determine an extent of similarity between the distributions;

rank the metrics based on the extent of similarity between the distributions belonging to the metrics, wherein metrics associated with distributions having less similarity rank higher than metrics associated with distributions having more similarity; and select the wavelengths of radiation associated with the higher ranked metrics.

\* \* \* \* \*